US011333336B1

(12) United States Patent
Tobin et al.

(10) Patent No.: US 11,333,336 B1
(45) Date of Patent: May 17, 2022

(54) PORTABLE LAMP ASSEMBLY

(71) Applicant: OPTICAL TOOLS LLC, Newton Highlands, MA (US)

(72) Inventors: Stephen M. Tobin, Newton, MA (US); Paul A. Sowyrda, Medfield, MA (US)

(73) Assignee: OPTICAL TOOLS LLC, Newton Highlands, MA (US)

( * ) Notice: Subject to any disclaimer, the term of this patent is extended or adjusted under 35 U.S.C. 154(b) by 0 days.

(21) Appl. No.: 17/412,779

(22) Filed: Aug. 26, 2021

(30) Foreign Application Priority Data

Aug. 20, 2021 (DE) ..................... 20 2021 104 495.0
Aug. 25, 2021 (DE) ..................... 20 2021 104 578.7

(51) Int. Cl.
*F21V 21/26* (2006.01)
*F21V 17/16* (2006.01)
*F21V 21/14* (2006.01)
*F21V 23/00* (2015.01)
*F21V 23/04* (2006.01)
*F21V 29/67* (2015.01)
*G01J 1/44* (2006.01)
*G01J 1/08* (2006.01)
*A61N 5/06* (2006.01)
*F21V 17/02* (2006.01)
*F21Y 115/10* (2016.01)
(Continued)

(52) U.S. Cl.
CPC ............ *F21V 21/26* (2013.01); *A61N 5/0616* (2013.01); *F21V 17/02* (2013.01); *F21V 17/16* (2013.01); *F21V 21/145* (2013.01); *F21V 23/003* (2013.01); *F21V 23/0471* (2013.01); *F21V 29/67* (2015.01); *G01J 1/08* (2013.01); *G01J 1/44* (2013.01); *A61N 2005/005* (2013.01); *A61N 2005/007* (2013.01); *A61N 2005/0626* (2013.01); *A61N 2005/0634* (2013.01); *A61N 2005/0642* (2013.01); *A61N 2005/0652* (2013.01); *A61N 2005/0663* (2013.01); *F21Y 2113/10* (2016.08); *F21Y 2115/10* (2016.08)

(58) Field of Classification Search
CPC ........ F21V 21/26; F21V 21/145; F21V 29/67; F21V 17/02; F21V 17/16; F21V 23/003; F21V 23/0471; A61N 5/0616; G01J 1/08; G01J 1/44
USPC .................................................... 362/249.03
See application file for complete search history.

(56) References Cited

U.S. PATENT DOCUMENTS 1,847,051 A 2/1932 Zabach
1,859,601 A 5/1932 Rice
(Continued)

*Primary Examiner* — Bryon T Gyllstrom
(74) *Attorney, Agent, or Firm* — Price Heneveld LLP

(57) ABSTRACT

A portable lamp assembly includes a spine member, a first and second side panel rotatably connected to the spine member, and a pair of first and second tangent links prismatically and rotatably operably coupled to the first and second side panel. Each of the tangent links has a plurality of vertical adjustment positions disposed between an upper and lower portion. The spine member and the first and second side panels have at least one source of light connected thereto. The first side panel and the second side panel can be rotated between an open position to allow the sources of light emit light towards a target area and a closed position for storage of the portable lamp assembly. The portable lamp assembly is free standing in the open position to allow the portable lamp assembly to be used without any external support.

39 Claims, 16 Drawing Sheets

(51) Int. Cl.
*F21Y 113/10* (2016.01)
*A61N 5/00* (2006.01)

(56) References Cited

U.S. PATENT DOCUMENTS

| | | | |
|---|---|---|---|
| D260,176 S | 8/1981 | Boschetti et al. | |
| 4,444,189 A | 4/1984 | Seiverd | |
| 4,523,256 A | 6/1985 | Small | |
| 4,581,684 A * | 4/1986 | Mazzucco | F21V 17/007 |
| | | | 362/183 |
| 4,680,681 A | 7/1987 | Fisherman et al. | |
| 5,379,201 A * | 1/1995 | Friedman | F21V 33/0052 |
| | | | 362/191 |
| 5,919,217 A * | 7/1999 | Hughes | A61M 21/00 |
| | | | 607/90 |
| 6,022,119 A * | 2/2000 | Booty, Jr. | F21V 27/00 |
| | | | 362/419 |
| 6,171,331 B1 | 1/2001 | Bagraev et al. | |
| 6,171,332 B1 | 1/2001 | Whitehurst | |
| 6,176,598 B1 | 1/2001 | Seligman | |
| 6,290,713 B1 | 9/2001 | Russell | |
| 6,419,370 B1 | 7/2002 | Chen | |
| 6,596,016 B1 | 7/2003 | Vreman et al. | |
| 6,602,275 B1 | 8/2003 | Sullivan | |
| 6,645,230 B2 | 11/2003 | Whitehurst | |
| 6,702,837 B2 | 3/2004 | Gutwein | |
| D496,396 S | 9/2004 | Hyman | |
| 6,835,202 B2 | 12/2004 | Harth et al. | |
| D503,426 S | 3/2005 | Chou | |
| 6,896,693 B2 | 5/2005 | Sullivan | |
| D509,014 S | 8/2005 | Bonneville | |
| 7,517,101 B2 * | 4/2009 | Tobin | A61N 5/0616 |
| | | | 362/1 |
| D661,329 S * | 6/2012 | Hui | D16/135 |
| 11,199,318 B2 * | 12/2021 | Liu | F21S 6/003 |
| 11,199,320 B1 * | 12/2021 | Chiu | F21V 29/67 |
| 2004/0093043 A1 | 5/2004 | Edel et al. | |
| 2005/0134524 A1 | 6/2005 | Parker et al. | |

* cited by examiner

PORTABLE LAMP ASSEMBLY

CROSS-REFERENCE TO FOREIGN PRIORITY APPLICATION

The present application claims the benefit under 35 U.S.C. §§ 119(b), 119(e), 120, and/or 365(c) of DE 20 2021 104 495.0 filed Aug. 20, 2021, and of DE 20 2021 104 578.7 filed Aug. 25, 2021.

FIELD OF THE INVENTION

The present invention concerns a lamp assembly for treating human skin disease and cosmetic abnormalities, and more particularly relates to a portable lamp assembly.

BACKGROUND OF THE INVENTION

Using light to treat human skin disease and cosmetic abnormalities (e.g., acne) is well known to those skilled in the art. An apparatus is desired to allow the treatment of human skin disease and cosmetic abnormalities in an easier manner.

SUMMARY OF THE PRESENT INVENTION

An aspect of the present invention is to provide a portable lamp assembly comprising a spine member, a first side panel and a second side panel. The spine member has a spine member top side and a spine member bottom side, the spine member including at least one spine member source of light connected to the spine member bottom side of the spine member, the spine member also including a first side and a second side. The first side panel has a proximal edge operably and rotatably coupled to the first side of the spine member, the first side panel including a first side panel top side and a first side panel bottom side, the first side panel including at least one first side source of light connected to the first side panel bottom side of the first side panel. A first tangent link is operably and rotatably coupled to the first side panel, the first tangent link having a lower portion at a distal end thereof for support of the first side panel on a surface, an upper portion, and a plurality of vertical adjustment positions disposed between the upper portion and the lower portion. A second side panel has a proximal edge operably and rotatably coupled to the second side of the spine member, the second side panel including a second side panel top side and a second side panel bottom side, the second side panel including at least one second side source of light connected to the second side panel bottom side of the second side panel. A second tangent link is operably and rotatably coupled to the second side panel, the second tangent link having a lower portion at a distal end thereof for support of the second side panel on the surface, an upper portion, and a plurality of vertical adjustment positions disposed between the upper portion and the lower portion. The first side panel and the second side panel can be rotated in a first direction relative to the spine member to arrange the portable lamp assembly in an open position to allow the at least one spine member source of light, the at least one first side source of light and the at least one second side source of light to emit light towards a target area. The first side panel and the second side panel can be rotated in a second direction relative to the spine member to arrange the portable lamp assembly in a closed position for storage of the portable lamp assembly. The portable lamp assembly is free standing in the open position to allow the portable lamp assembly to be used without any external support. The relative height of each of the first and second side panels relative the surface may adjusted by selection of a one of the plurality of vertical adjustment positions of each of the first and second tangent links.

Another aspect of the present invention is to provide a spine member having a spine member top side and a spine member bottom side, the spine member including at least one spine member source of light connected to the spine member bottom side of the spine member, the spine member also including a first side and a second side, a first side panel rotatably connected to the first side of the spine member, the first side panel including a first side panel top side and a first side panel bottom side, the first side panel including at least one first side source of light connected to the first side panel bottom side of the first side panel, and a second side panel rotatably connected to the second side of the spine member, the second side panel including a second side panel top side and a second side panel bottom side, the second side panel including at least one second side source of light connected to the second side panel bottom side of the second side panel. A pair of first tangent links attached to the first side panel between an upper portion and a lower portion of the pair of first tangent links, whereby each of the first tangent links is operably coupled to a one of a pair of opposite sides of first side panel, and a pair of second tangent links attached to the second side panel between the upper portion and a lower portion of the pair of second tangent links, whereby each of the second tangent links is operably coupled to a one of a pair of opposite sides of the second side panel. The portable lamp assembly can be placed in an open position with the lower portion of the first tangent link and the second tangent link resting on a support surface and with the spine member, the first side panel and the second side panel being spaced from the support surface.

A further aspect of the present invention is a portable lamp assembly comprising a spine member having a spine member top side and a spine member bottom side, the spine member including at least one spine member source of light connected to the spine member bottom side of the spine member, the spine member also including a first side and a second side. A first side panel is rotatably connected to the first side of the spine member, the first side panel including a first side panel top side and a first side panel bottom side, the first side panel including at least one first side source of light connected to the first side panel bottom side of the first side panel. A second side panel is rotatably connected to the second side of the spine member, the second side panel including a second side panel top side and a second side panel bottom side, the second side panel including at least one second side source of light connected to the second side panel bottom side of the second side panel. A pair of first tangent links is attached to the first side panel between an upper portion and a lower portion of the pair of first tangent links, whereby each of the first tangent links is prismatically and rotatably operably coupled to a one of a pair of opposite sides of first side panel, and the first tangent link has a lower portion at a distal end thereof for support of the first side panel on a surface, an upper portion, and a plurality of vertical adjustment positions disposed between the upper portion and the lower portion. A pair of second tangent links is attached to the second side panel between the upper portion and a lower portion of the pair of second tangent links, whereby each of the second tangent links is prismatically and rotatably operably coupled to a one of a pair of opposite sides of the second side panel, and the second tangent link has a lower portion at a distal end thereof for support of the first side panel on the surface, an upper portion, and a plurality of vertical adjustment positions disposed between the upper portion and the lower portion. A pair of block detent assemblies by which the first side panel and the second side panel are rotatably and operably coupled is to the spine member, the pair of block detent assemblies comprising a plurality of recesses arranging in a semicircular pattern disposed on the spine member or proximate the proximal side of each of the first side panel or the second side panel; and a spring loaded detent disposed on the other of the spine member or proximate the proximal side of each of the first side panel or the second side panel. The portable lamp assembly can be placed in an open position with the lower portion of the first tangent link and the second tangent link resting on a support surface and with the spine member, the first side panel and the second side panel being spaced from the support surface, and wherein a relative height of each of the first side panel and the second side panel relative the surface may adjusted by selection of a one of the plurality of vertical adjustment positions of each of the first and second tangent links. The detent is selectively disposed within one of the plurality of recesses for securing the spine member relative the first side panel and the second side panel when the portable lamp assembly is in use.

These and other aspects, objects, and features of the present invention will be understood and appreciated by those skilled in the art upon studying the following specification, claims, and appended drawings.

DETAILED DESCRIPTION OF PREFERRED EMBODIMENTS

Figure 1:
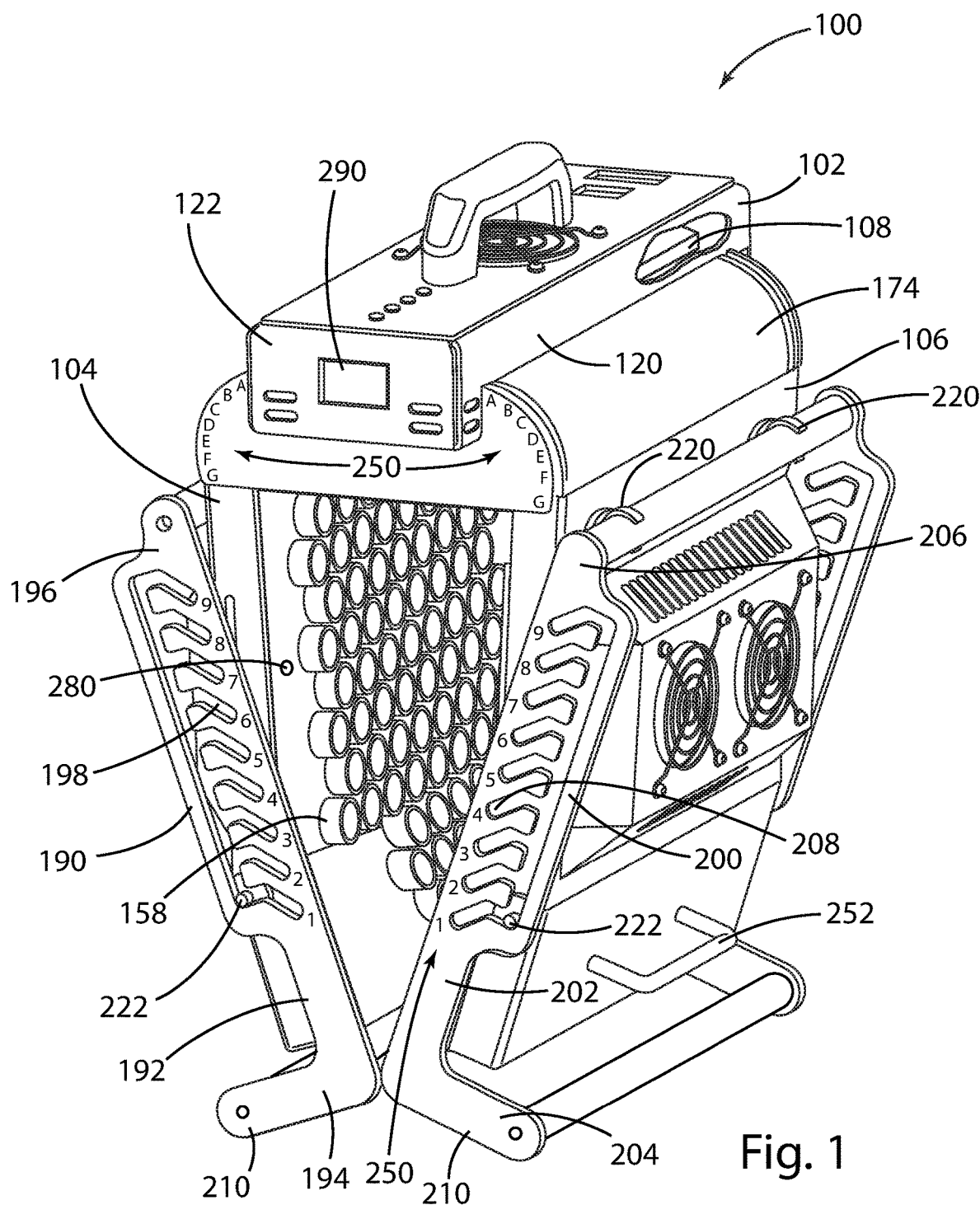
FIG. 1 is a perspective view of a portable lamp assembly of the present invention in a closed position.

For purposes of description herein, the terms "upper," "lower," "right," "left," "rear," "front," "vertical," "horizontal," and derivatives thereof shall relate to the invention as orientated in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention is an improvement over U.S. Pat. No. 7,517,101, entitled Convertible Lamp Array and issued on Apr. 14, 2009, naming the present inventors, which is hereby incorporated by reference as though fully set forth herein.

Reference number 100 (FIGS. 1-2) generally designates the portable lamp assembly embodying the present invention. The portable lamp assembly 100 represents a compact and easily mobile light source platform for wound healing, acne, and is compatible for use with ALA and M-ALA drug types in photo-dynamic therapy.

In the illustrated example, the portable lamp assembly 100 comprises a spine member 102, a first side panel 104, and a second side panel 106, with the first side panel 104 and the second side panel 106 being rotatably and operably coupled to the spine member 102. A central control box 108 may be housed within the spine member.

The spine member 102 may be constructed as a rectangular prism having a spine member top side 110 and a spine member bottom side 112. A carrying handle 114 may be disposed on the spine member top side 110. The spine member 102 includes at least one spine member source of light 116 connected to the spine member bottom side 108. The spine member 102 also includes a spine member first side 118, a spine member second side 120, a spine member front side 122, and a spine member rear side 124. A desirable longitudinal length of the spine member 102 is about 12 inches (30 cm), with a height of about 2⅞ inch (7 cm) and a width of about 7⅞ inch (12 cm).

The first side panel 104 may also be constructed as a rectangular prism and has a first side panel top side or shroud 126 and a first side panel bottom side 128. The first side panel 104 includes at least one first side source of light 130 connected to the first side panel bottom side 128. The first side panel 104 also includes a first side panel proximal side 132, a first side panel distal side 134, a first side panel front side 136, and a first side panel rear side 138. A desirable longitudinal length of the first side panel 104 is about 9⅞ inches (25 cm), with a thickness of about 2 inch (5 cm) and a width of about 10⁷⁄₁₆ inch (27 cm). The first side panel 104 has a proximal edge 140 operably and rotatably coupled to the spine member first side 118, as further described below.

The second side panel 106 may be identical in shape to the first side panel 104. It has a second side panel top side or shroud 142 and a second side panel bottom side 144. The second side panel 106 includes at least one second side source of light 146 connected to the second side panel bottom side 144. The second side panel 106 likewise includes a second side panel proximal side 148, a second side panel distal side 150, a second side panel front side 152, and a second side panel rear side 154. The second side panel 106 may be identical in size to the first side panel 104. The second side panel 106 has a proximal edge 156 operably and rotatably coupled to the spine member 102, as further described below.

The portable lamp assembly 100 may be used to treat human skin disease and cosmetic abnormalities (e.g., acne) using light alone or in other manners as is well known to those skilled in the art. It is also contemplated that the portable lamp assembly 100 could be used for mood improvement, wound healing (as is well known to those skilled in the art), sun tanning, or curing various items (e.g., epoxies).

Figure 2:
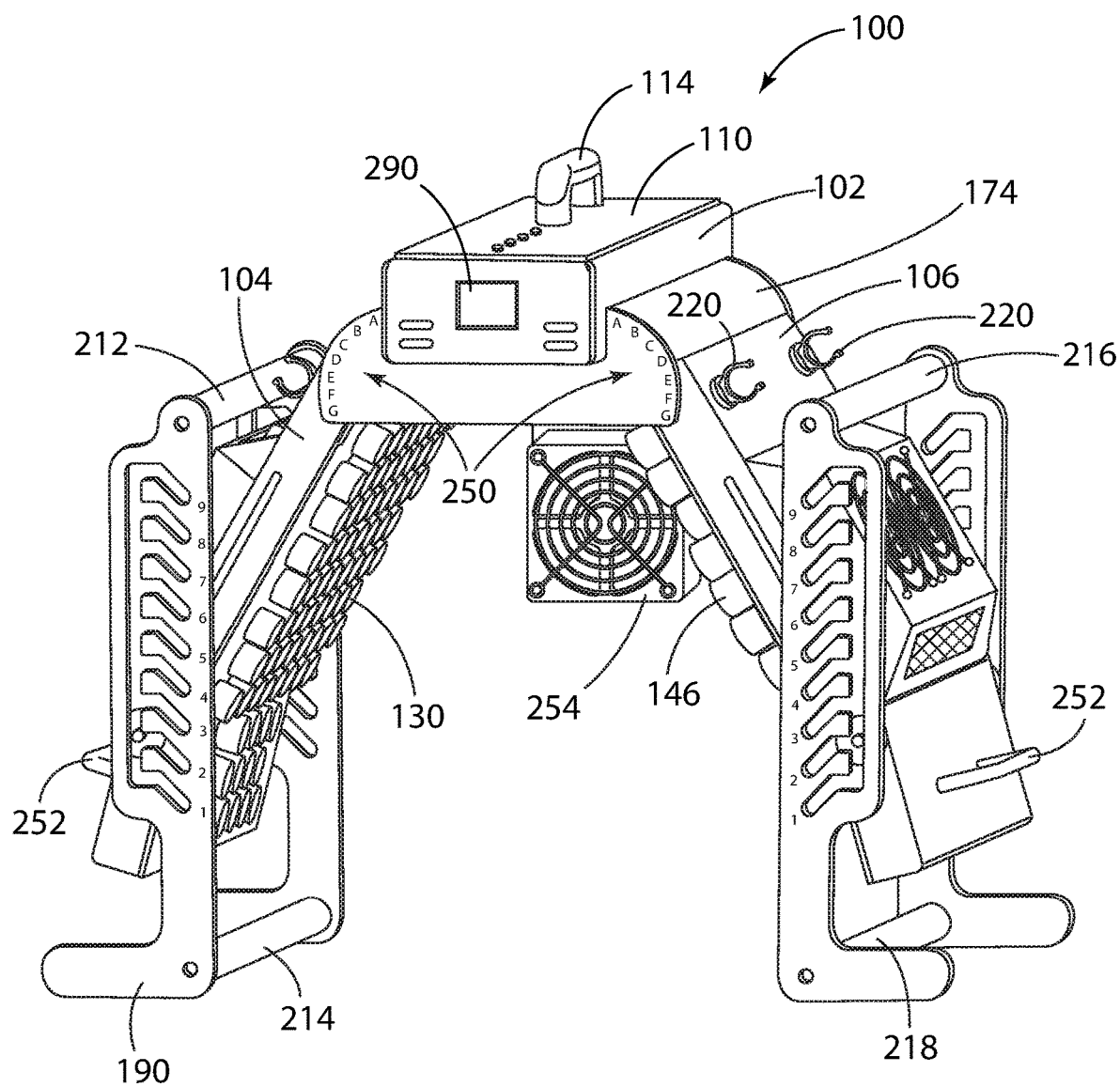
FIG. 2 is a perspective view of the portable lamp assembly of the present invention in a partially open position.
Figure 3:
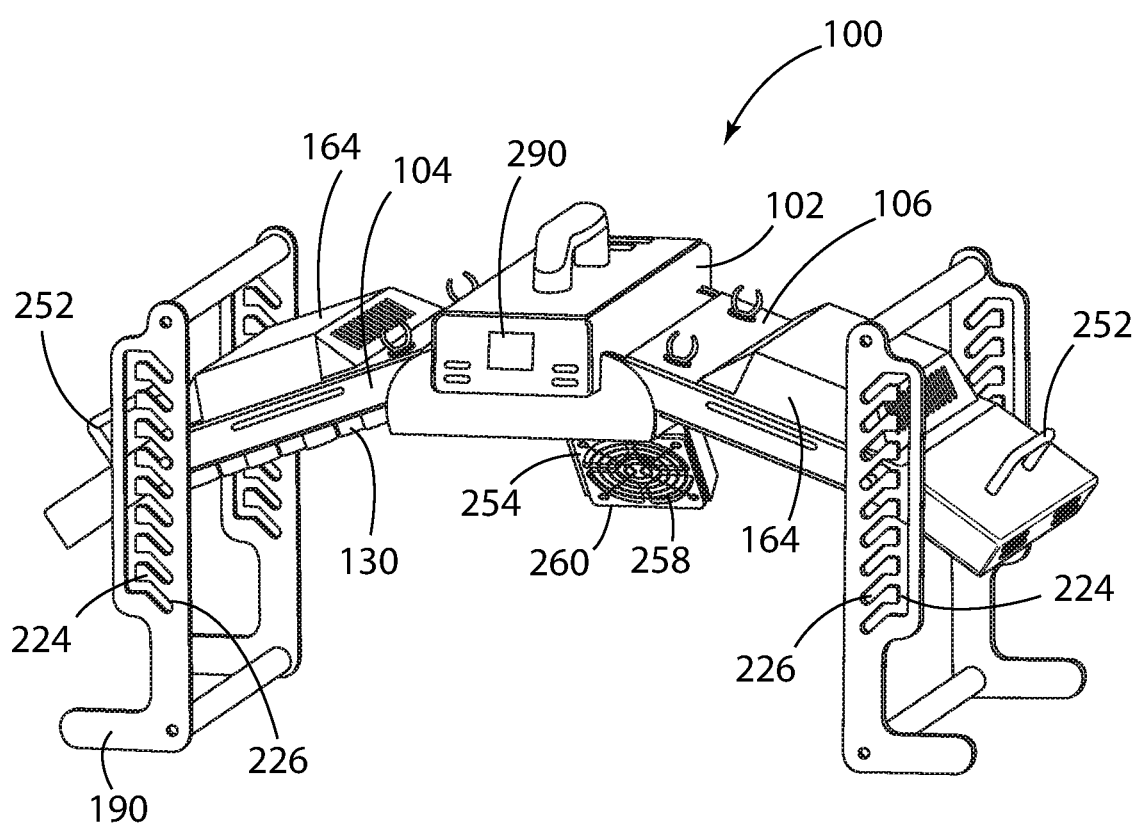
FIG. 3 is a perspective view of the portable lamp assembly of the present invention in a fully open position.

The at least one spine member source of light 116 connected to the spine member bottom side 108, the at least one first side source of light 130 connected to the first side panel bottom side 128, and the at least one second side source of light 146 connected to the second side panel bottom side 144 may comprise a plurality of individual electrical light sources, particularly light emitting diodes 145, packaged in individual light housings 158 further comprising an optic (not shown) to focus the emitted light arranged as an array on each of the spine member bottom side 108, the first side panel bottom side 128, and the second side panel bottom side 144, as shown in FIGS. 1-3.

The light sources described herein may be adapted to emit light in the red electromagnetic wavelengths between 550-750 nm, particularly 630 nm, +/−5 nm. Alternatively, the light sources described herein may be adapted to emit light in the "blue" (violet) electromagnetic wavelengths between 350-450 nm, particularly 415 nm, +/−5 nm. The light sources described herein may emit at a power intensity of substantially 60 mW/cm2, +/−15% at 630 nm or 10 mW/cm2, +/−15% at 415 nm.

Figure 8:
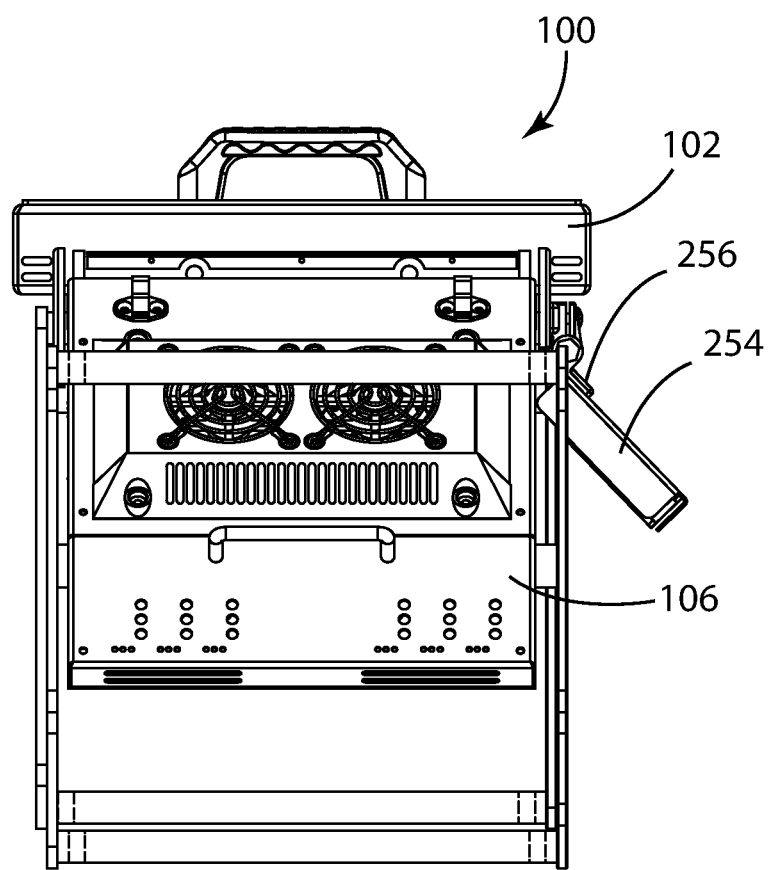
FIG. 8 is a side view of the portable lamp assembly of the present invention shown in FIG. 6.
Figure 9:
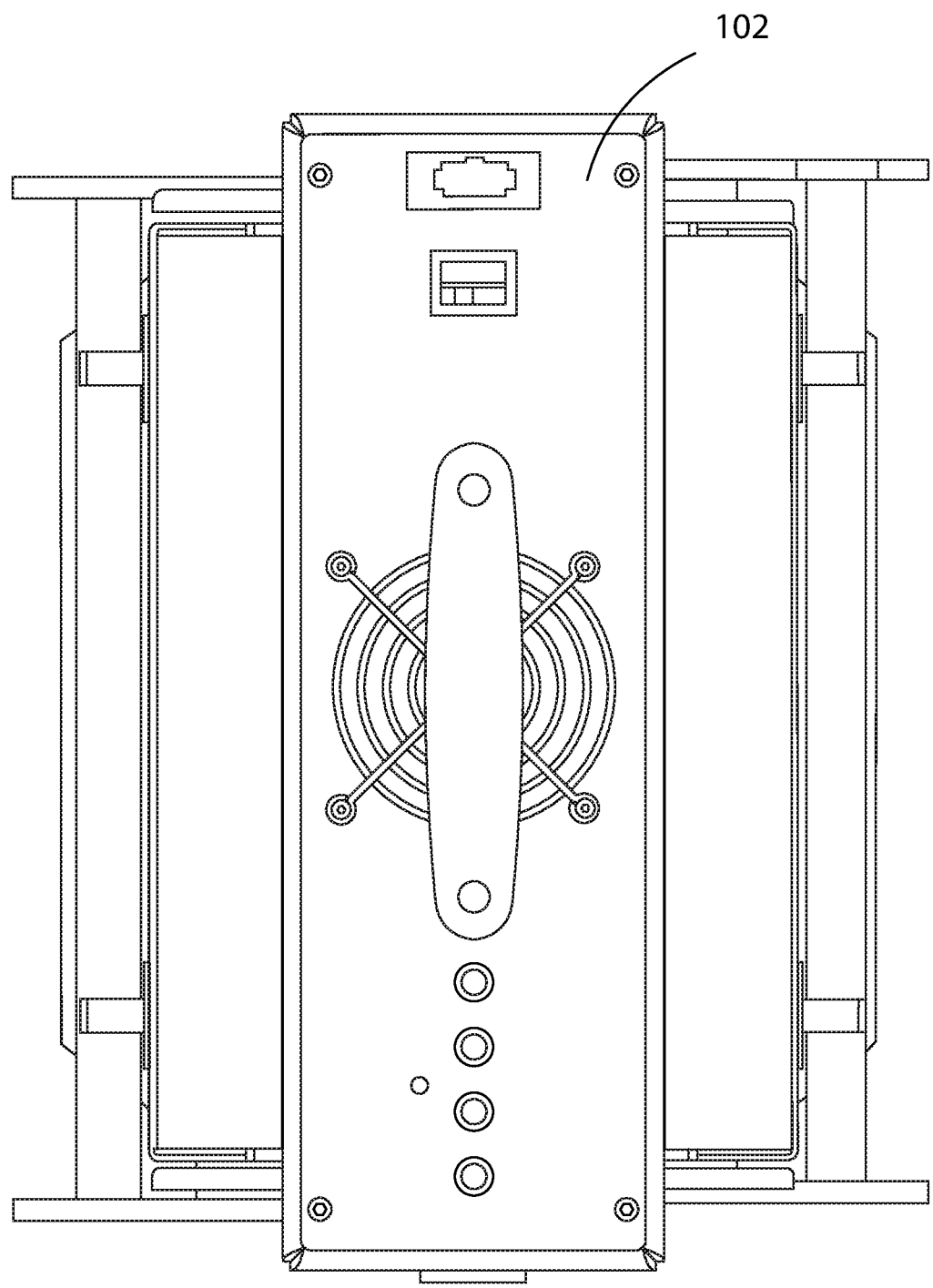
FIG. 9 is a top view of the portable lamp assembly of the present invention in the folded and stored position shown in FIG. 1.

As shown in the Figures, a portion of the light emitting diodes 145 are arranged in a plurality of rows disposed on each of the first side panel bottom side 128 and the second side panel bottom side 144, wherein the intensity of one of the plurality of rows of light emitting diodes 145 may be individually adjustable. The intensity of one of the plurality of rows of light emitting diodes 145 may be individually adjustable by a potentiometer (not shown) accessible by openings 160 on the first side panel top side 126 and the second side panel top side 142. Alternatively, the intensity of each of the plurality of rows of light emitting diodes 145 may be individually adjustable by a potentiometer accessible by the opening 160 on the first side panel top side 126 and the second side panel top side 142. Three to six partial rows of light emitting diodes 145 may be provided proximate the distal side 134, 150 on of the bottom side 128, 144 of the side panels 104, 106 to fully treat the ears, as shown in FIG. 8. For example, two separate grouping of three partial rows of three light emitting diodes 145 may be provided.

The dosage provided by the light emitting diodes 145 may be 37 J/cm$^2$ nominal (for 600 seconds). The treatment distance may be 2 inches to 3 inches (5 to 7.5 cm) and thereby treat an area of about 10×20 inches$^2$ (25×50 mm$^2$).

The light emitting diodes 145 are deployed on the underside of the spine member 102 and side panels 104, 106 in an array of patterns based on the wavelength of light emitted necessary to achieve uniformity of plus or minus 20% over the treatment area and distance. The disclosed portable lamp assembly 100 can be opened to a wide range of discrete arcs. Since the lamp arrays are on the undersides of the spine member 102 and both side panels 104, 106, it can treat wider and larger areas (such as the back or chest), or rounded body areas (such as the scalp or the face).

A cooling fan assembly 162 comprising a pair of fans, such as Model 19155k94 offered by Delta Electronica (Americas) Ltd., and a shroud 164 may be disposed on each of the first top side 126 and the second top side 142 of each of the first and second side panels 104, 106, respectively, as shown in FIG. 3, whereby cooling air is directed to the one first side source of light 130 and the one second side source of light 146. Use of the cooling fan assembly 162 may allow the use of more intense illumination of the source of light 130, 146 by providing a positive air flow through each of the first and second side panels 104, 106.

Figure 10:
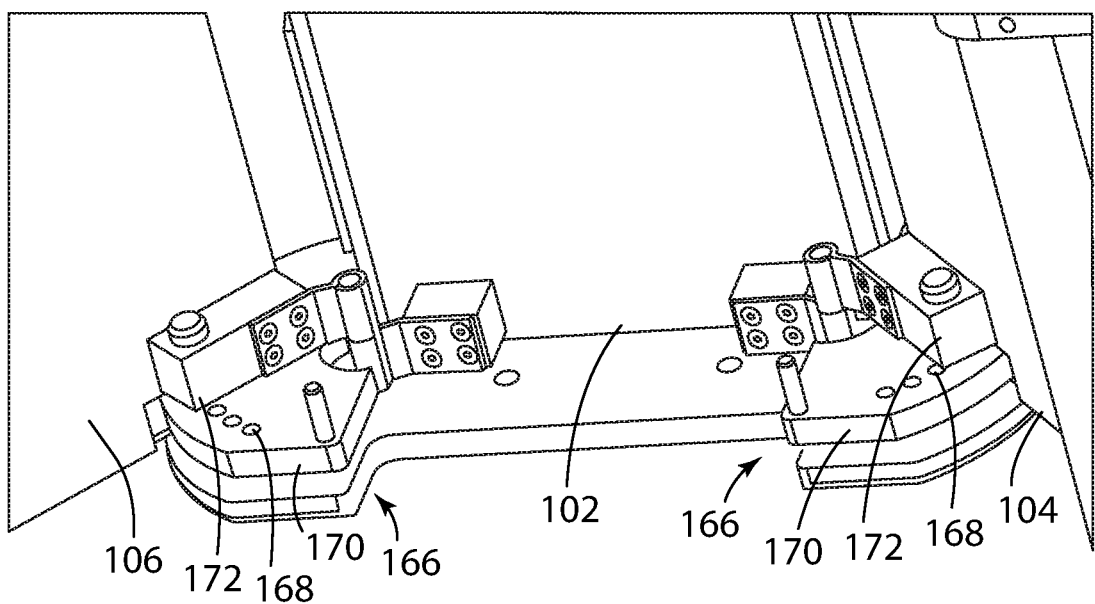
FIG. 10 is a bottom perspective view of the bottom perspective view of the spine member with the light sources omitted and the block detent assemblies of the present invention.

In the illustrated example, the first side panel 104 and the second side panel 106 are rotatably attached to the spine member by pair of block detent assemblies 166, best shown in FIG. 10, each comprising a plurality of recesses 168 arranging in a semi-circular pattern on a hinge block 170 disposed on the spine member 102 or proximate the proximal side 132, 148 of each of the first or second side panels 104, 106, and a spring loaded detent 172 disposed on the other of the spine member 102 or proximate the proximal side 132, 148 of each of the first or second side panels 104, 106. Any number of recesses 168 may be provided to obtain the desired angle and height range, although seven detents 172 has been found to be most appropriate. The detent 172 may be selectively disposed within one of the plurality of recesses 168 for securing the spine member 102 relative the first and second side panels 104, 106 when the portable lamp assembly is in use.

As a consequence of the use of the block detent assemblies 166, the height of the spine member 102 and each of the proximal edges 140, 156 of the first and second side panels 104, 106 may be elevated to the height of the light emitting diode optics disposed on the bottom side 128, 144 of the first and second side panels 104, 106 to eliminate gaps when the first and second panels 104, 106 are rotated for use.

The portable lamp assembly 100 of the present disclosure overcomes the problem of prior devices that were unable to cover the whole face, including up to the ears. By adopting the hinged patient fan assembly 260, to be described, it is now possible to add light emitting diodes 145 to the ear areas.

Figure 4:
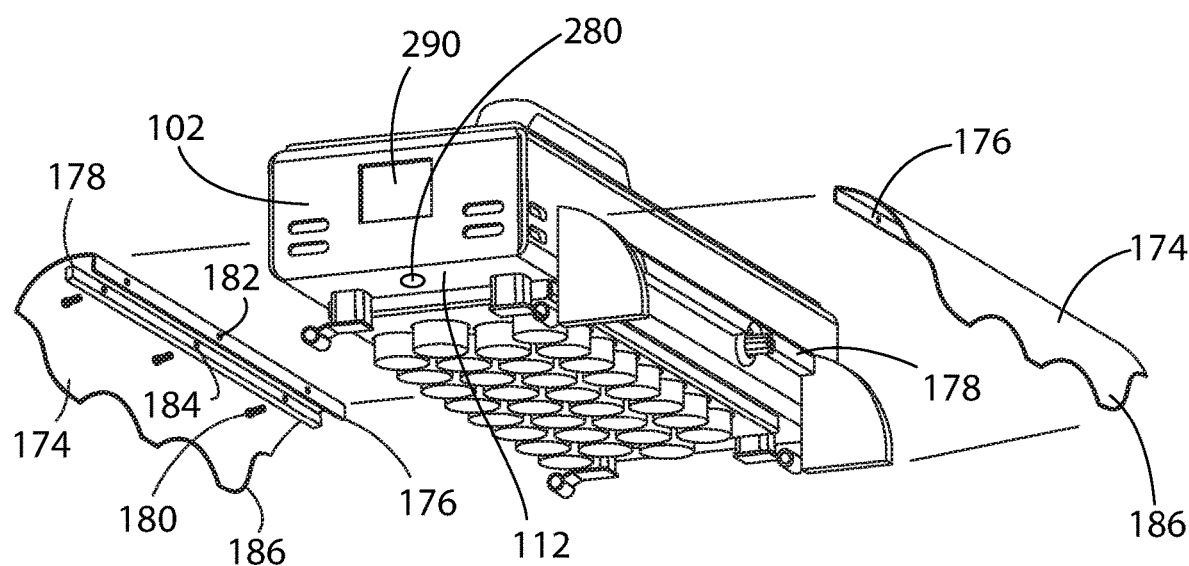
FIG. 4 is a bottom perspective view of the spine member and the finger guards of the portable lamp assembly of the present invention.
Figure 5:
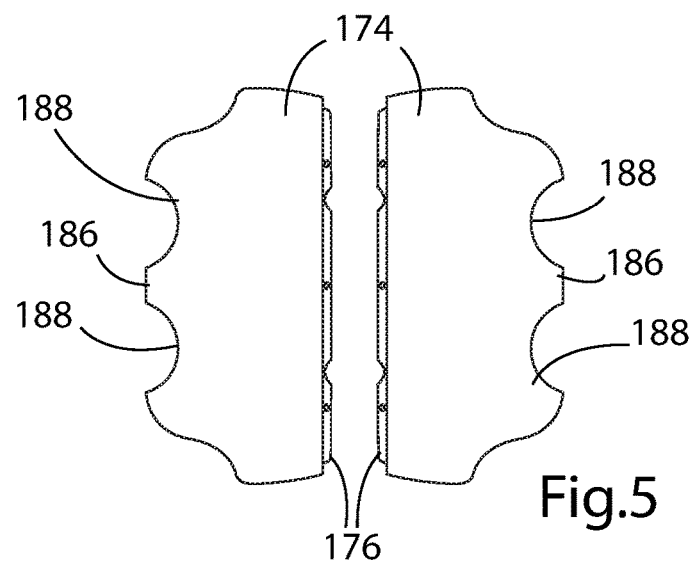
FIG. 5 is a top plane of the finger guards of the portable lamp assembly of the present invention.
Figure 6:
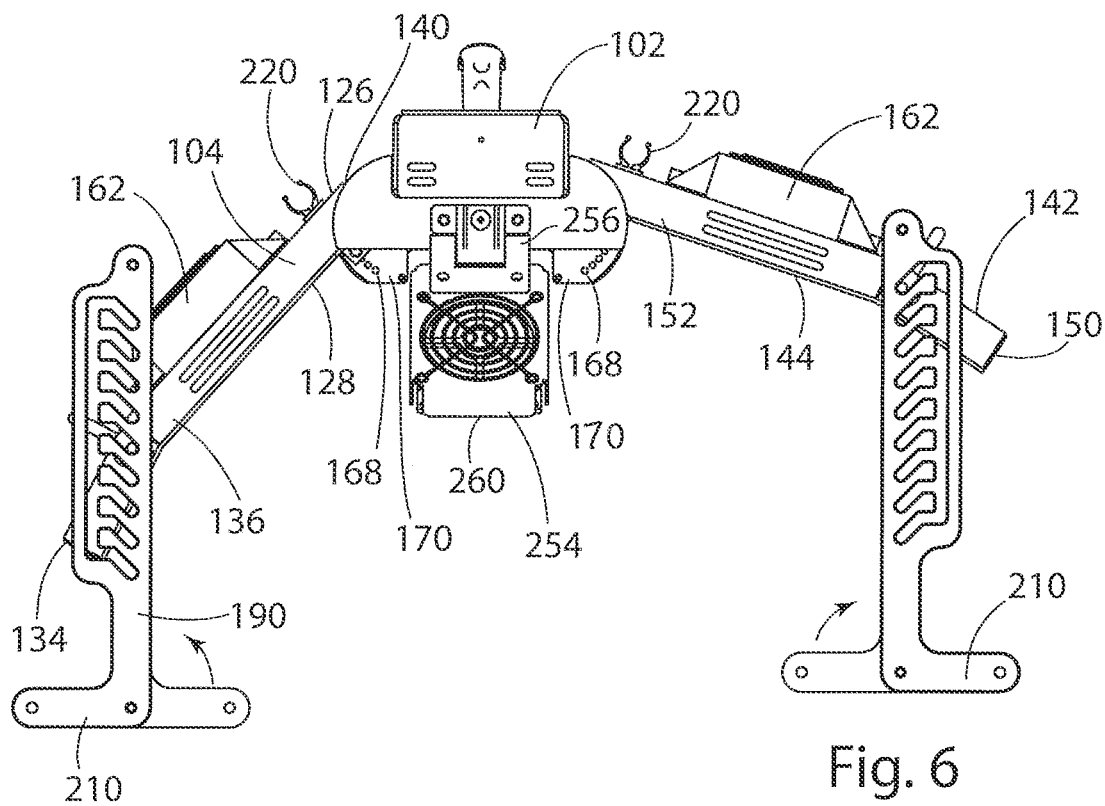
FIG. 6 is a front plan view of the portable lamp assembly of the present invention, with the light sources omitted and with a first side panel adjusted at a lower position than a second side panel.
Figure 7:
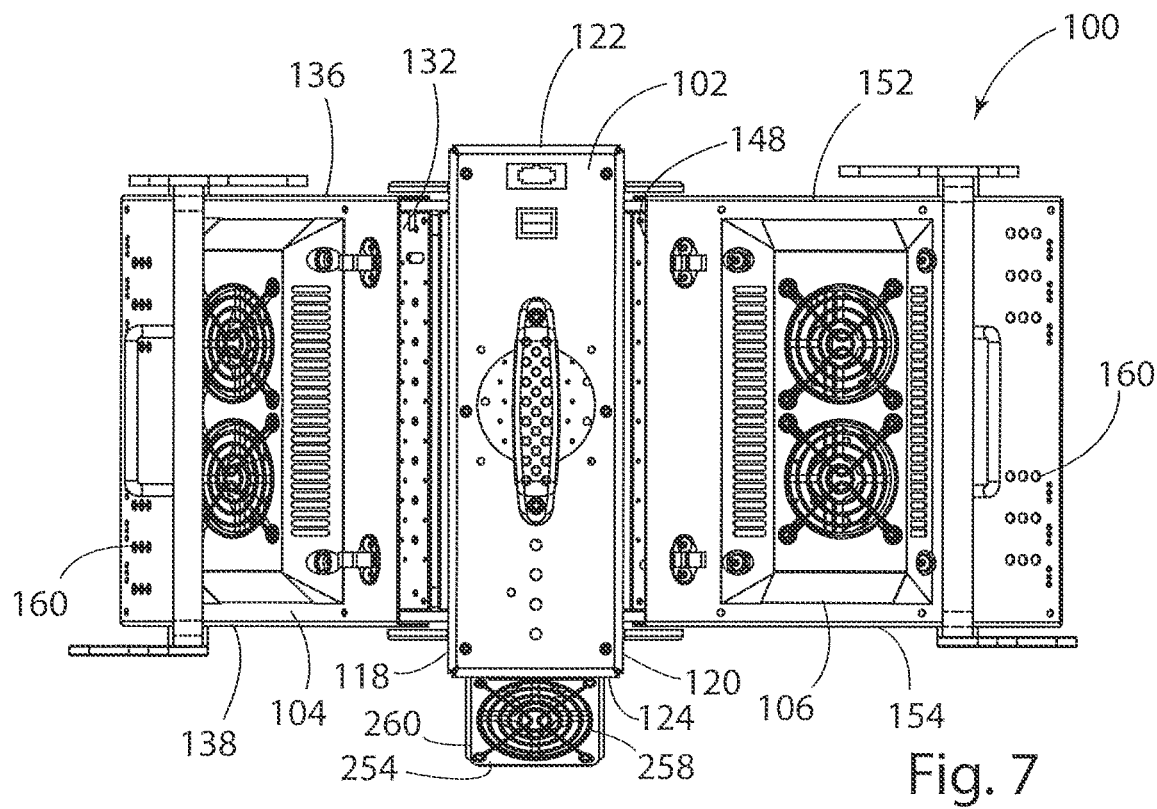
FIG. 7 is a top view of the portable lamp assembly of the present invention shown in FIG. 6.

As shown in FIGS. 1-3, a pair of finger guards 174 may be provided proximate a hinge line defined between the spine member 102 and each of the proximal side 132, 148 of the first and second side panels 104, 106 to prevent the fingers of the operator or patient from becoming pinched within the hinge line. As illustrated in FIG. 4, an upper edge 176 of each of the pair of finger guards 174 may be clamped by a finger guard mount 178 operably coupled to each of the first and second side 118, 120 of the spine member 102. That is, a plurality of threaded fasteners 180 may be passed through openings 184 in the finger guard mount 178, through openings 182 in the upper edge 176 of each of the pair of finger guards 174, and then into threaded openings (not shown) in the first and second sides 118, 120 of spine member 102 to secure the finger guard mount 178 to the spine member 102. Alternatively, the plurality of threaded fasteners 180 may be passed through openings (not shown) in the first and second sides 118, 120 of spine member 102, from inside the spine member 102, and through openings 182 in the upper edge 176 of each of the pair of finger guards 174. The fasteners 180 may then be received into threaded openings 184 in the finger guard mount 178 to secure the finger guard mount 178 to the spine member 102.

The pair of finger guards 174 are then flexed and a lower edge 186 of each finger guard 174 may be tucked below the proximal edge 140, 156 of each of the first and second side panels 104, 106, and adjacent the bottom side 128, 144 of each of the first and second side panels 104, 106, respectively. Recesses 188 are provided on the lower edge 186 of each finger guard 174, such that the air provided by the pair of cooling fan assembly 162 disposed on each of the top side 126, 142 of each of the first and second side panels 104, 106 is not obstructed. The pair of finger guards 174 may be made from a flexible polymeric material, such as polyester. It must be thick enough not to bunch when tucked into position, but thin enough to maintain sufficient flexibility to do so, such as a thickness of 0.024 to 0.048 inches (1.0 to 2 mm).

A first tangent link 190 is prismatically and rotatably operably coupled to the first side panel 104. By prismatically, it is meant that the coupling allows linear translating motion. Thus, the first tangent link 190 is coupled to the first side panel 104 so as to allow translational and rotational degrees of freedom of movement relative each other. The first tangent link 190 has a lower portion 192 at a distal end 194 thereof for support of the first side panel 104 on a surface, an upper portion 196, and a plurality of vertical adjustment positions 198 disposed between the lower portion 192 and the upper portion 196. A second tangent link 200 is likewise prismatically and rotatably operably coupled to the second side panel 106, the second tangent link 200 having a lower portion 202 at a distal end 204 thereof for support of the second side panel 106 on the surface, an upper portion 206, and a plurality of vertical adjustment positions 208 disposed between the upper portion 206 and the lower portion 202.

Each of the first and second tangent links 190, 200 may include a cleat 210 extending orthogonally with respect to a vertical longitudinal axis of the first and second tangent links 190, 200. The cleat 210 may face outwardly, as shown in FIGS. 1-3, which facilitates folding of the portable lamp assembly 100, or inwardly. The cleat 210 may be fixed, as shown, or the cleat 210 may be rotatably and operably coupled with the lower portion 192, 202 of each of the first and second tangent links 190, 200 and rotatable between a first position extending orthogonally with respect to a vertical longitudinal axis of the first and second tangent links 190, 200 and a second position extending upwardly and parallel to the vertical longitudinal axis of the first and second tangent links 190, 200. Dedicated bumpers (not shown) may be provided on the cleat 210 of the tangent links to enhance stability.

The portable lamp assembly 100 may include a pair of first tangent links 190 attached to the first side panel 104 between the lower portion 192 and upper portion 196 of the pair of first tangent links 190, as shown in FIGS. 1-3, whereby each of the first tangent links 190 is operably coupled to a one of a pair of opposite sides of the first side panel 104, that is, the first side panel front side 136 and the first side panel rear side 138. A pair of second tangent links 200 is similarly attached to the second side panel 106 between the lower portion 202 and upper portion 206 of the pair of second tangent links 200, whereby each of the second tangent links 190, 200 is operably coupled to a one of a pair of opposite sides of the second side panel 106, that is, the second side panel front side 152 and the second side panel rear side 154. Each of the pairs of first and second tangent links 190, 200 are first mirror image of each other.

A first upper crosslink member 212 extends between the upper portion 196 of each of the pair of first tangent links 190 and a first lower crosslink member 214 extends between the lower portion 192 of each of the pair of first tangent links 190, while a second upper crosslink member 216 extends between the upper portion 206 of each of the pair of second tangent links 200 and a second lower crosslink member 218 extends between the lower portion 202 of each of the pair of second tangent links 200. A resilient clip 220 may be the first and second side panel top sides 126, 142, above the cooling fan assembly 162, wherein the first and second upper crosslink members 212, 216 may be retained by the clips 220 on in the stored position, as shown in FIG. 1. A pair of spaced resilient clips 220 may be the first and second side panel top sides 126, 142, wherein the first and second upper crosslink members 212, 216 are retained by the pair of clips 220 on in a stored position.

A plurality of pivot mounts 222 may be provided, wherein a one of the plurality of pivot mounts 222 is disposed on each of the first side panel front side 136, the first side panel rear side 138, the second side panel front side 152, and the second side panel rear side 154. One of the plurality of pivot mounts 222 engages a one of the plurality of vertical adjustment positions 198, 208 disposed between the lower and upper portions 196, 206 of the pairs of first and second tangent links 190, 200, respectively.

The plurality of vertical adjustment positions 198, 208 disposed between the lower and upper portions 196, 206 of the pairs of first and second tangent links 190, 200 may comprise a vertically extending slot 224 and a plurality of inwardly and downwardly inclined notches 226 extending from the vertically extending slot 224, such as shown in FIGS. 1-3, wherein the plurality of pivot mounts 222 are disposed within the slot 12 for movement of the pairs of first and second tangent links 190, 200 relative the first or second side panel 104, 106 and the plurality of pivot mounts 222 are selectively disposed within one of the plurality of notches 226 for securing the one of the pairs of first and second tangent links 190, 200 relative the first or second side panel 104, 106 when the portable lamp assembly 100 is in use. Any number of notches 226 may be provided to obtain the desired height range, although nine notches 226 has been found to be most appropriate.

The pivot mounts 222 may simply comprise an outwardly extending pin, as shown in FIGS. 1-3. By use of the inwardly and downwardly inclined notches 226, extending diagonally relative the support surface, gravity may be employed to secure the portable lamp assembly 100.

Figure 11:
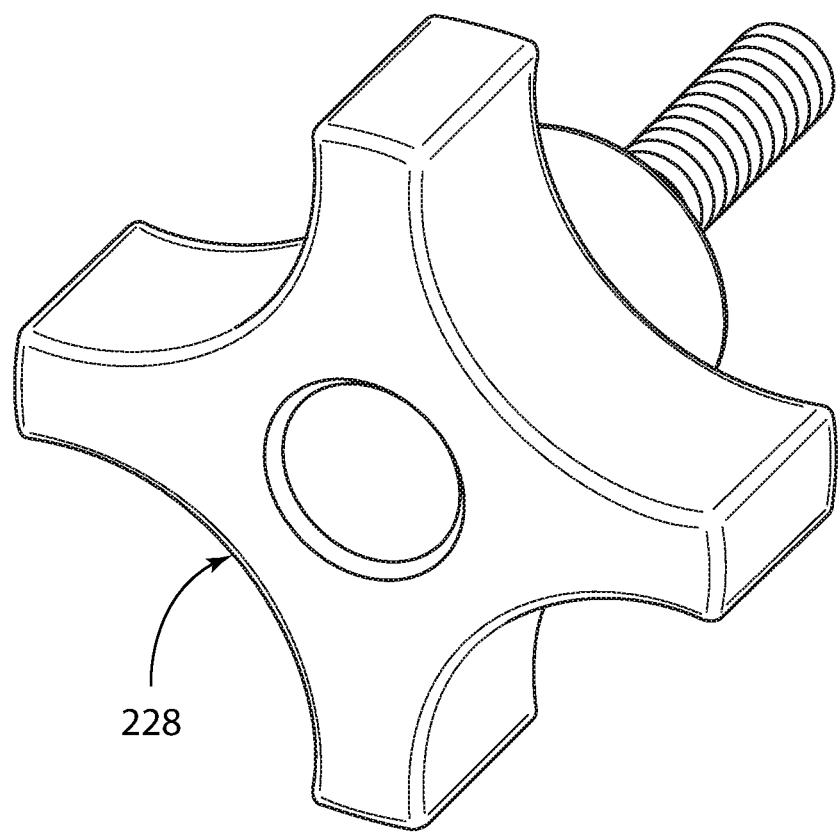
FIG. 11 is a perspective view of rotatable knob of the lamp assembly of the present invention.

However, a threaded and rotatable knob 228, as shown in FIG. 11, that extends into a threaded opening (not shown) in each of each of the first side panel front side 136, the first side panel rear side 138, the second side panel front side 152, and the second side panel rear side 154 is preferred in order to releasably secure the first and second tangent links 190, 200 to the first and second side panels 104, 106.

Figure 12:
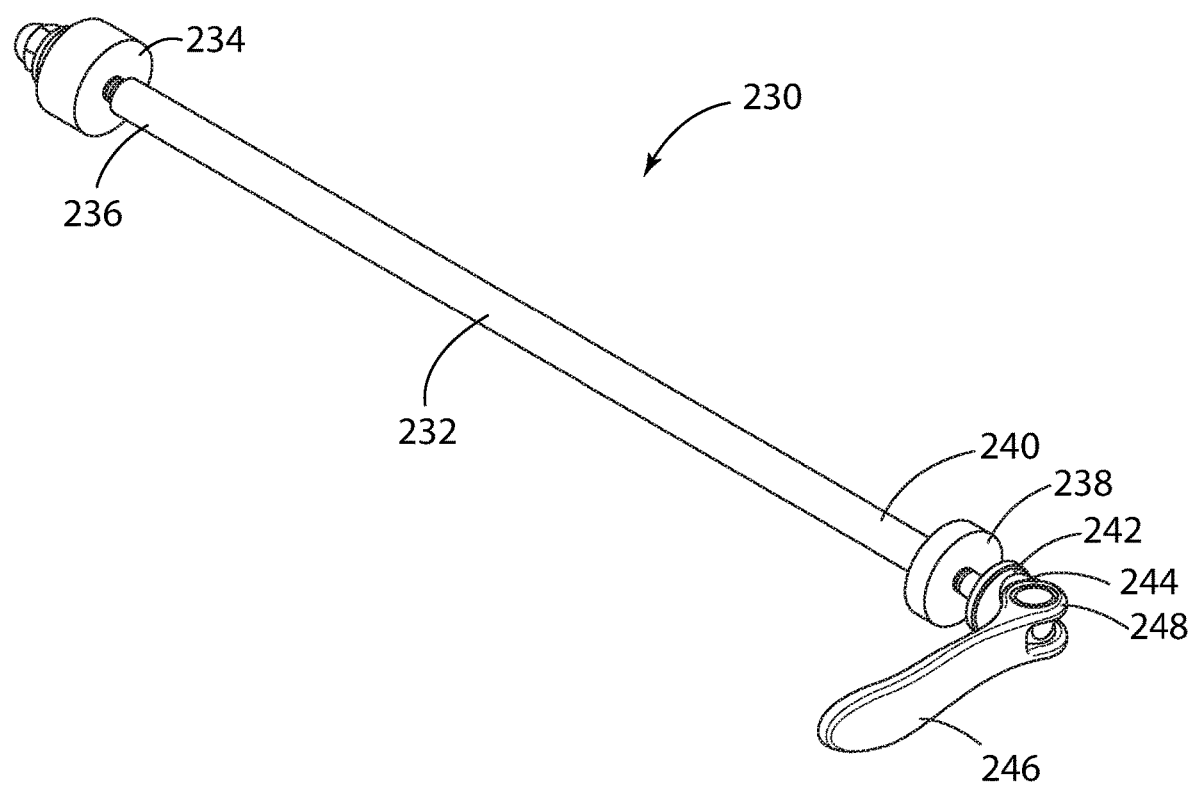
FIG. 12 is a perspective view of retaining clamp of the lamp assembly of the present invention.

Alternatively, a retaining clamp 230, as shown in FIG. 12, may be inserted into a passageway (not shown) extending through each of the first and second side panels 104, 106. The retaining clamp 230 may comprise a longitudinally extending bar 232, a retaining stop 234 threaded onto a first distal end 236 of the bar 232, and a clamp member 238 threaded onto a proximal end 240 of the bar 232. The clamp member 238 further comprises a base 242 having curvilinear recess 244 and a rotatable handle 246 having a curvilinear pivot mount 248. In operation, the bar 232 is inserted through each of the plurality of vertical adjustment positions 198, 208 disposed on the first and second tangent links 190, 200 and through the passageway. The retaining stop 234 may be attached, and then the clamp member 238 may be attached and threaded onto the bar 232 until snug. The rotatable handle 246 may then be rotated to clamp and lock the first and second tangent links 190, 200 relative the first and second side panels 104, 106.

In order to facilitate repeatable deployment of the portable lamp assembly 100, a unique position indicia 250 may be disposed proximate each of the plurality of vertical adjustment positions 198, 208 of the first and second tangent links 190, 200 and each of the plurality of recesses 168 of the block detent assemblies 166. The unique position indicia 250 disposed proximate each of the plurality of vertical adjustment positions 198, 208 of the first and second tangent links 190, 200 may be a visible number and the unique position indicia 250 proximate each of the plurality of recesses 168 of the block detent assemblies 166 may be a visible alphabetic letter. The unique position indicia 250 disposed proximate each of the plurality of vertical adjustment positions 198, 208 of the first and second tangent links 190, 200 may be stamped into (if metal), molded onto (if polymeric), or affixed by labels or other methods. The setting for an individual patient may thereby the charted so that the portable lamp assembly 100 may be accurately and repeatably set up for future visits.

The first side panel 104 and the second side panel 106 can thus be rotated in a first direction relative to the spine member 102 to arrange the portable lamp assembly 100 in an open position to allow the at least one spine member source of light 116, the at least one first side source of light 130, and the at least one second side source of light 146 to emit light towards a target area, as shown in FIGS. 2 and 3. The first side panel 104 and the second side panel 106 can be rotated in a second direction relative to the spine member 102 to arrange the portable lamp assembly 100 in a closed position for storage of the portable lamp assembly 100, as shown in FIG. 1. Accordingly, the portable lamp assembly 100 is free standing in the open position to allow the portable lamp assembly 100 to be used without any external support, wherein the relative height of each of the first and second side panels 104, 106 relative the surface may adjusted by selection of a one of the plurality of vertical and horizontal adjustment positions 198, 208 of each of the first and second tangent links 190, 200.

A pair of handles 252 may be provided, where one each of the pair of handles 252 may be disposed on each of the first and second top sides 126 142 of each of the first and second side panels 104, 106, whereby each of the first and second side panels 104, 106 may be manipulated between an open position with the lower portions 192, 202 of the first and second tangent links 190, 200 resting on a support surface and with the spine member 102, the first side panel 104 and the second side panel 106 being spaced from the support surface.

The portable lamp assembly 100 may also include a patient fan assembly 254, such as offered by Delta Electronica (Americas) Ltd., rotatably and operably coupled with the rear end of the spine member 102 for providing the patient being treated with air ventilation. The patient fan assembly 254 may be rotated over 180 degrees between a substantially upward vertical position and substantially downward vertical position. The patient fan assembly 254 may be fabricated from sheet metal and may be operably coupled with the spine member with adjustable torque hinges 256, such as adjustable torque hinge, Model E6-10-501-10, available from Southco, Inc., which are symmetric, large size, and fabricated of acetal copolymer. The patient fan assembly 254 may be provided with a finger guard 258 to prevent the patient's or operator's fingers from entering the path of the fan blade, which may comprise radially spaced concentric metal rings. The patient fan assembly 254 so situated offers direct cooling to the scalp and face of the patient. The patient fan assembly 254 so situated also offers the ability to tip the portable lamp assembly 100 so that when the patient fan assembly 254 is rotated partially downward, portable lamp assembly 100 may be supported by corners between the distal side 134, 150 and the rear side 138, 154 of each of the first and second side panels 104, 106 and a distal end 260 of the patient fan assembly 254, thus providing enhanced treatment of a patient's head and scalp.

It is contemplated that the spine member 102, the first side panel 104, and the second side panel 106 could be made of any material that has the strength to support the entire partially downward, portable lamp assembly 100 (e.g., plastic). The block detent assemblies 166 and the first and second tangent links 190, 200 can be set at a selected position and easily maintained in that position until altered by a user of the portable lamp assembly 100.

Figure 13:
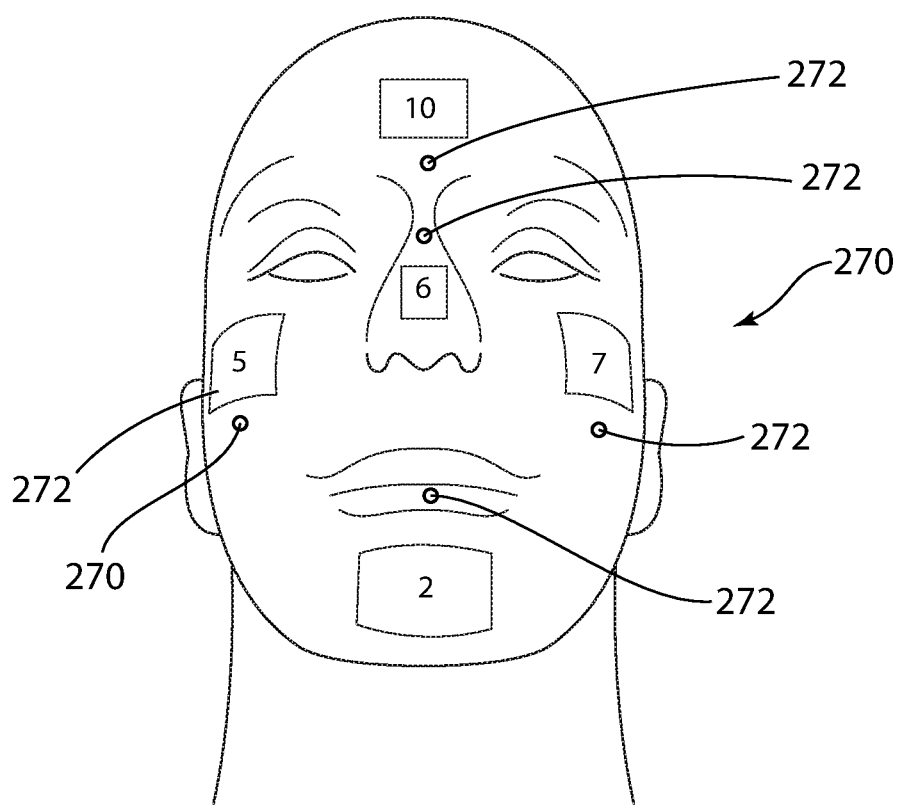
FIG. 13 is a front view of the phantom for use with the portable lamp assembly of the present invention.
Figure 14:
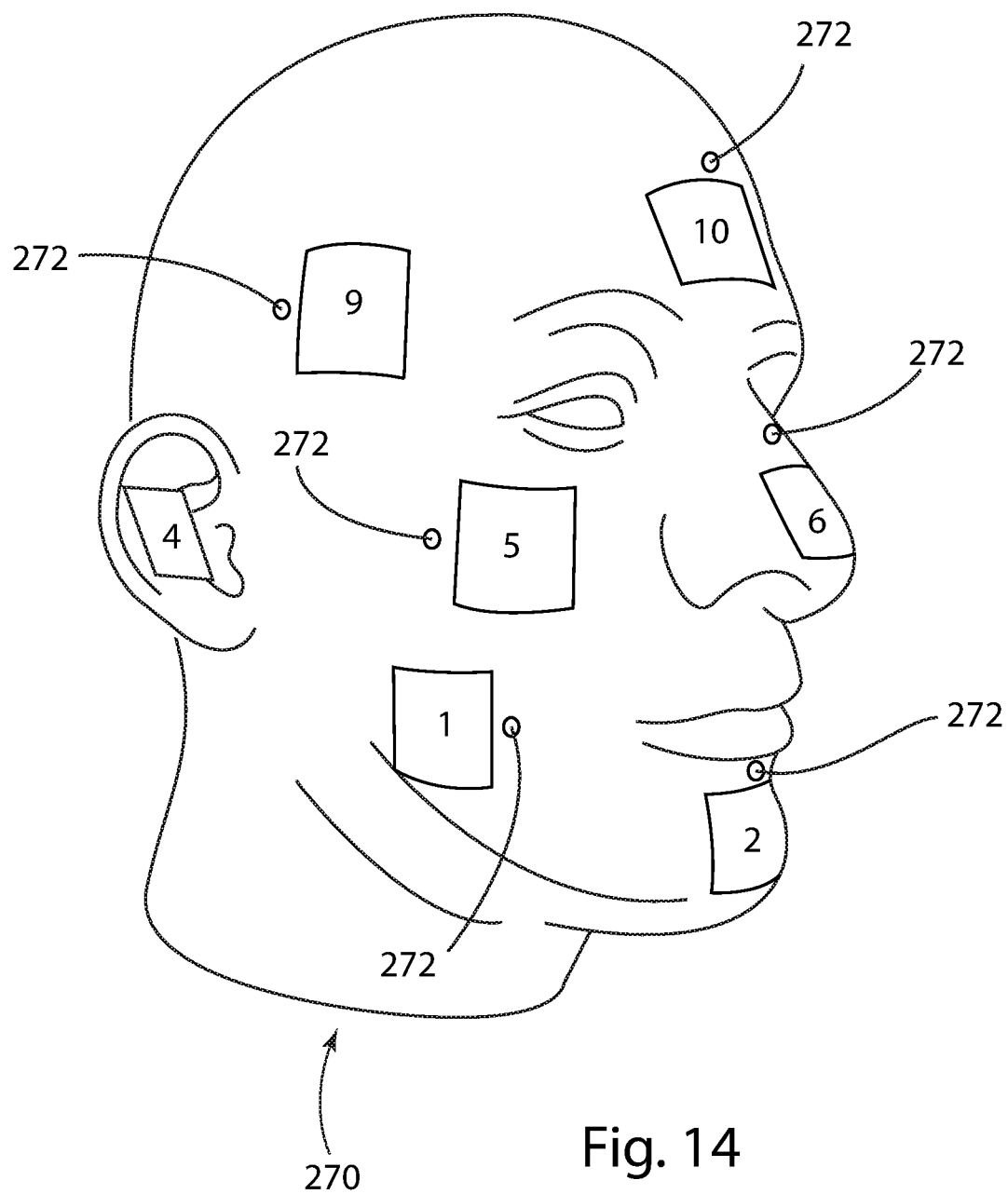
FIG. 14 is a first side view of the phantom for use with the portable lamp assembly of the present invention.
Figure 15:
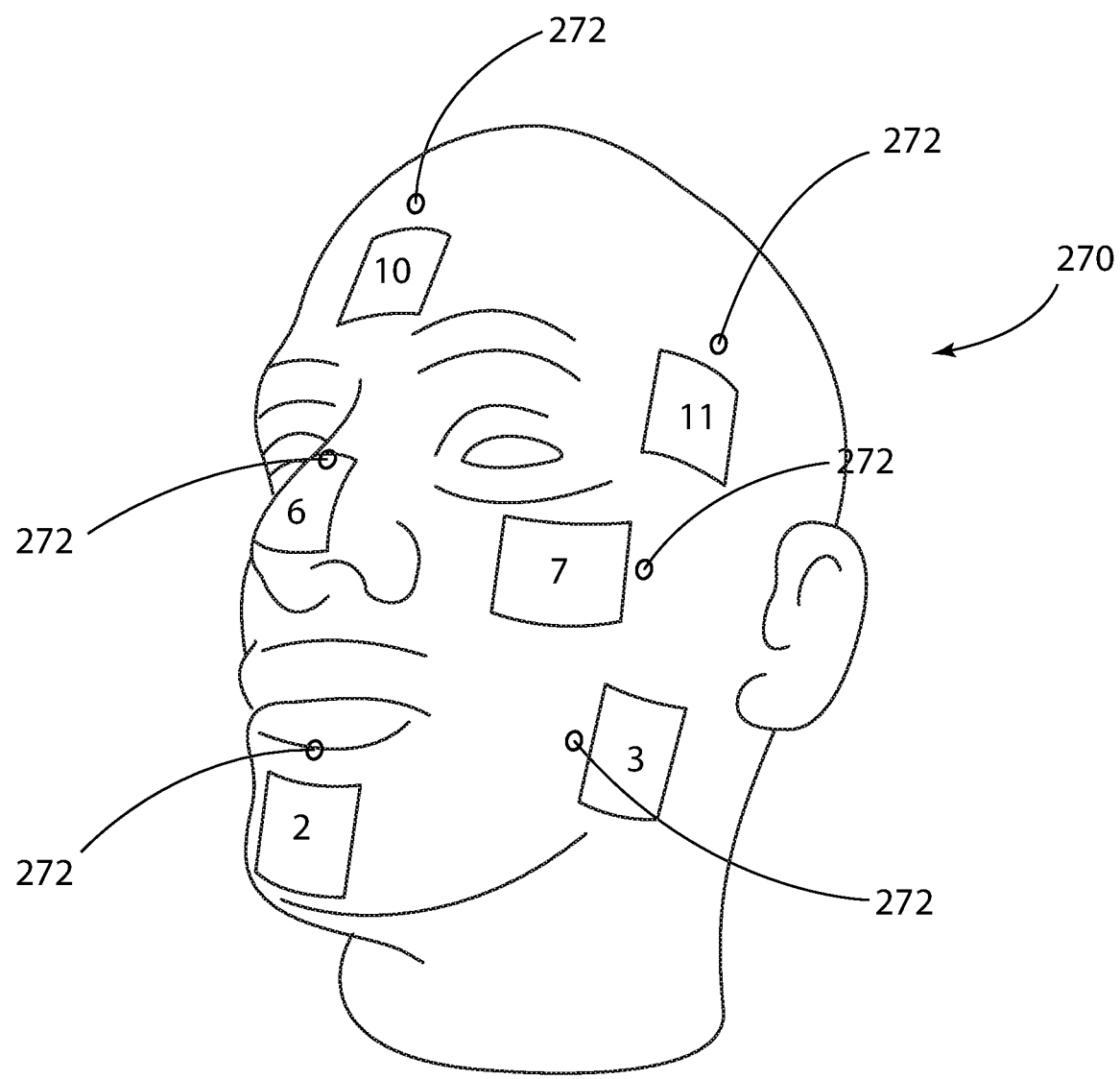
FIG. 15 is a second side view of the phantom for use with the portable lamp assembly of the present invention.

A further aspect of the present disclosure is self-calibration using a phantom 270 loaded with multiple photodetectors 272, as shown in FIGS. 13-15. The phantom 270 is essentially a model of the human head in which a plurality of light intensity photodetectors 272 are imbedded. As the light emitting diodes 145 in the spine member 102, the first side panel 104, and the second side panel 106 are actuated, the light intensity on the phantom 270 can be measured. The output of the light emitting diodes 145 can then be adjusted to provide a desired intensity at any particular location(s) on the phantom 270, as described above. It is contemplated that the output of multiple photodetectors 272 could be connected electronically to the timer microcontroller, and said microcontroller could be programmed to adjust the LED intensity automatically. Alternatively or in conjunction with an output adjustment, the height and angle of the side panels 104, 106 can be adjusted, as described above, to provide a desired intensity at any particular location(s) on the phantom 270. Thus, before the patient even arrives for treatment, the portable lamp assembly 100 can be set up and calibrated for the particular needs of that patient.

A further aspect of the present disclosure is the deployment of at least one and preferably three proximity sensors 280, situated on the bottom surface of the spine 112 and both surfaces of side panels 144. These sensors 280 are preferably electronically connected to the electronic timer microcontroller. Signals from the proximity sensors 280 could serve as an aid to the operator in achieving the proper distance from light emitting diode light housing 158 to the skin surface of the patient.

As shown in the Figures, a constant current source electronic circuit may be used to drive the light emitting diodes 145, in combination with a light emitting diode driver with a shut-down capability provided by a digital built-in timer, which may be connected to the spine member 102, the first side panel 104 or the second side panel 106 to display and control a duration of light exposure. Examples of the light emitting diode drivers may be found in the circuit diagrams depicted in FIGS. 16-18. The power supply to the constant current sources and timer may be 24 VDC regulated output, 100-240 VAC input, operating at 50-60 Hz and drawing about 4.0 A. Such a circuit provides more stable and controlled power.

Figure 16:
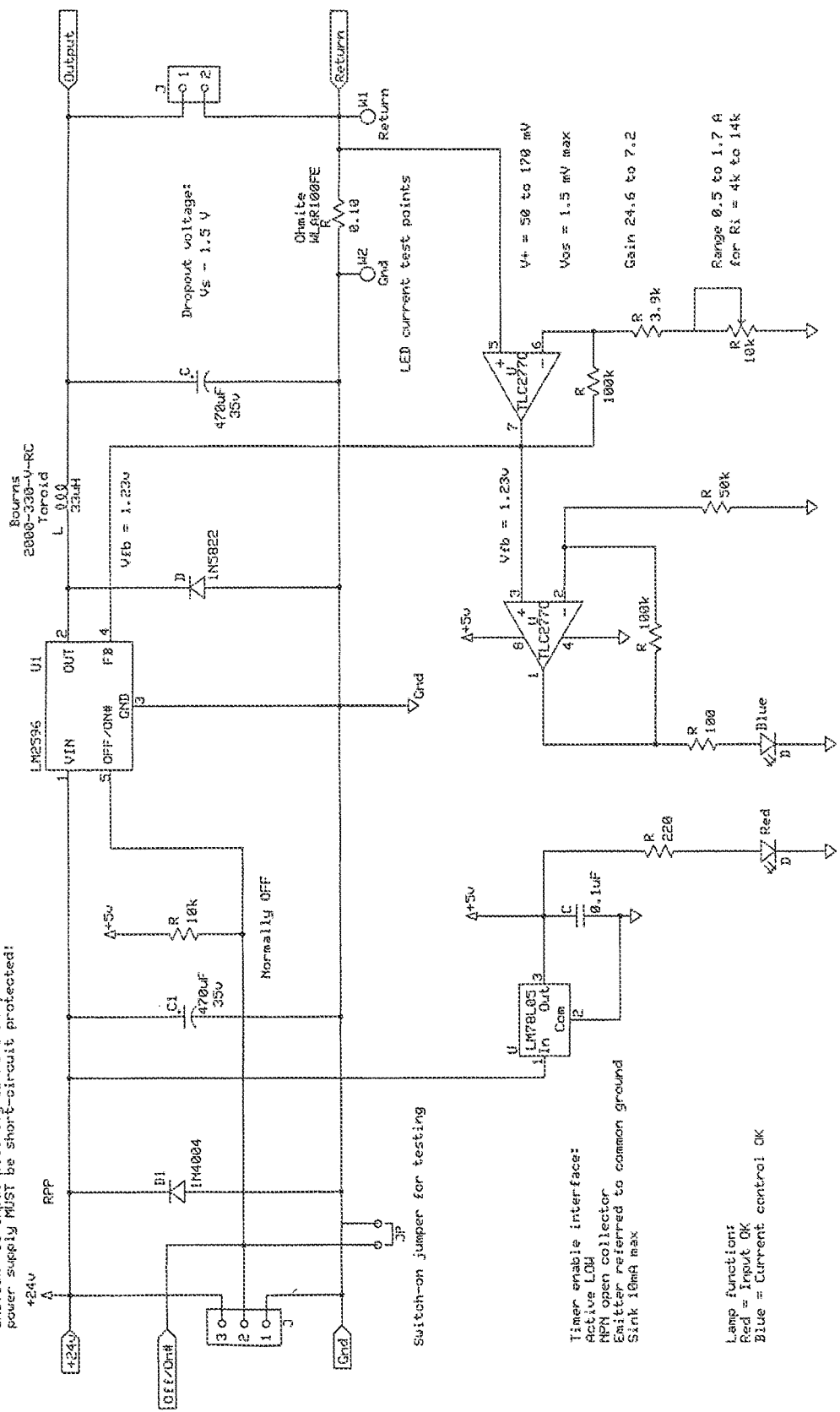
FIG. 16 is a circuit diagram of the light emitting diode driver circuit for the portable lamp assembly of the present invention.
Figure 17:
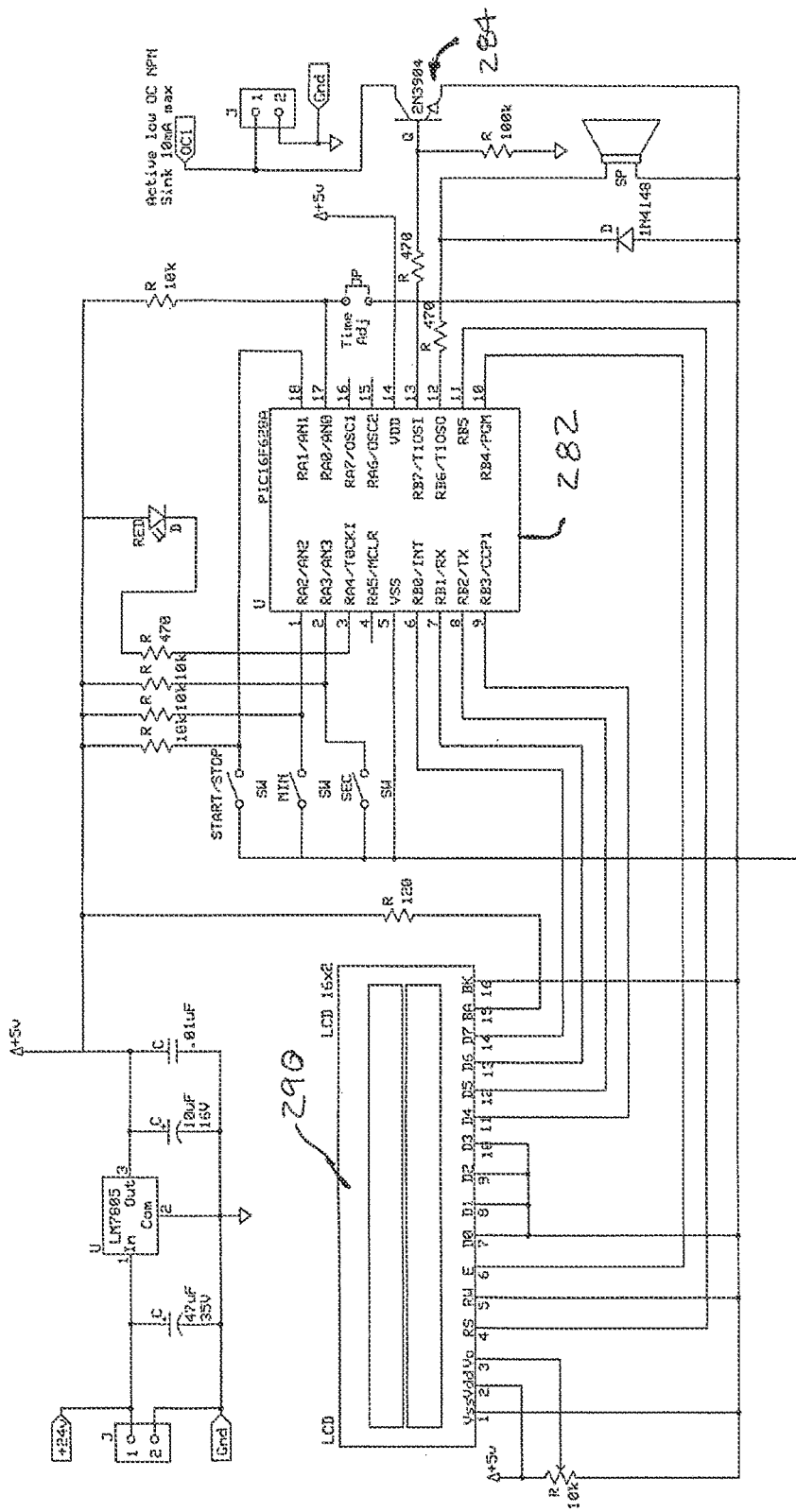
FIG. 17 is a circuit diagram of the timer circuit for the portable lamp assembly of the present invention.

As opposed to prior devices, a low-level signal LED on-off switching capability is provided instead of a relay, which might be difficult to procure at the rated DC switching current. That is, the circuit includes a switch mode buck converter operably coupled with a connector which regulates the voltage of the assembly 100, wherein the switch mode buck converter has an enable pin. As shown in FIG. 16, the driver control for the light emitting diodes 145 may be switched off by the timer portion of the circuit. An example of a light emitting diode driver having a digital built-in timer 282 may be found in the circuit diagram depicted in FIGS. 17 and 18. The digital built-in timer 282 may control a switching transistor 284 to provide the on/off control of the light emitting diodes 145. However, if desired, the digital timer with a relay output can be provided.

It is contemplated that the digital timer can be mounted to the spine member 102 (or other parts of the portable lamp assembly 100) to display and control duration of light exposure to the patient. A display 290 can be provided to indicate the number of minutes remaining in given treatment protocol. The timer may be adapted to provide up to 99 minutes, 59 seconds of treatment time. An alarm may be added to alert the operator that the treatment period has been reached.

A counter may be connected to the spine member 102, the first side panel 104 or the second side panel 106 to record and display the total number of hours that the sources of light have been powered. An example of such a display 290 may be found in the front panel of the spine member, as depicted in FIGS. 1 and 4.

Alternatively, an AC input power cord supplies alternating current to an isolated AC-to-DC adapter. Direct current at a voltage preferably at or below 48V is supplied through a direct current cable to the spine member. It is contemplated that the direct current cable may be connected or disconnected to the spine member with a detachable connector. The detachable connector is attached to the spine member to provide power distribution to a printed circuit board on the spine member. Other means of powering the portable lamp assembly 100 are contemplated (e.g., batteries).

The plurality of light emitting diodes 145 may be mounted on a printed circuit board, or directly onto side panels 144. However, it is contemplated that any light source that can treat human skin disease and cosmetic abnormalities could be used.

The plurality of light emitting diodes 145 may be connected in a series and parallel fashion. The values of the ballast resistors can be chosen to determine the current in any series chain of three light emitting diodes 145. A reverse polarity protection diode D1 (FIG. 16) may also be provided on the printed circuit board.

Figure 18:
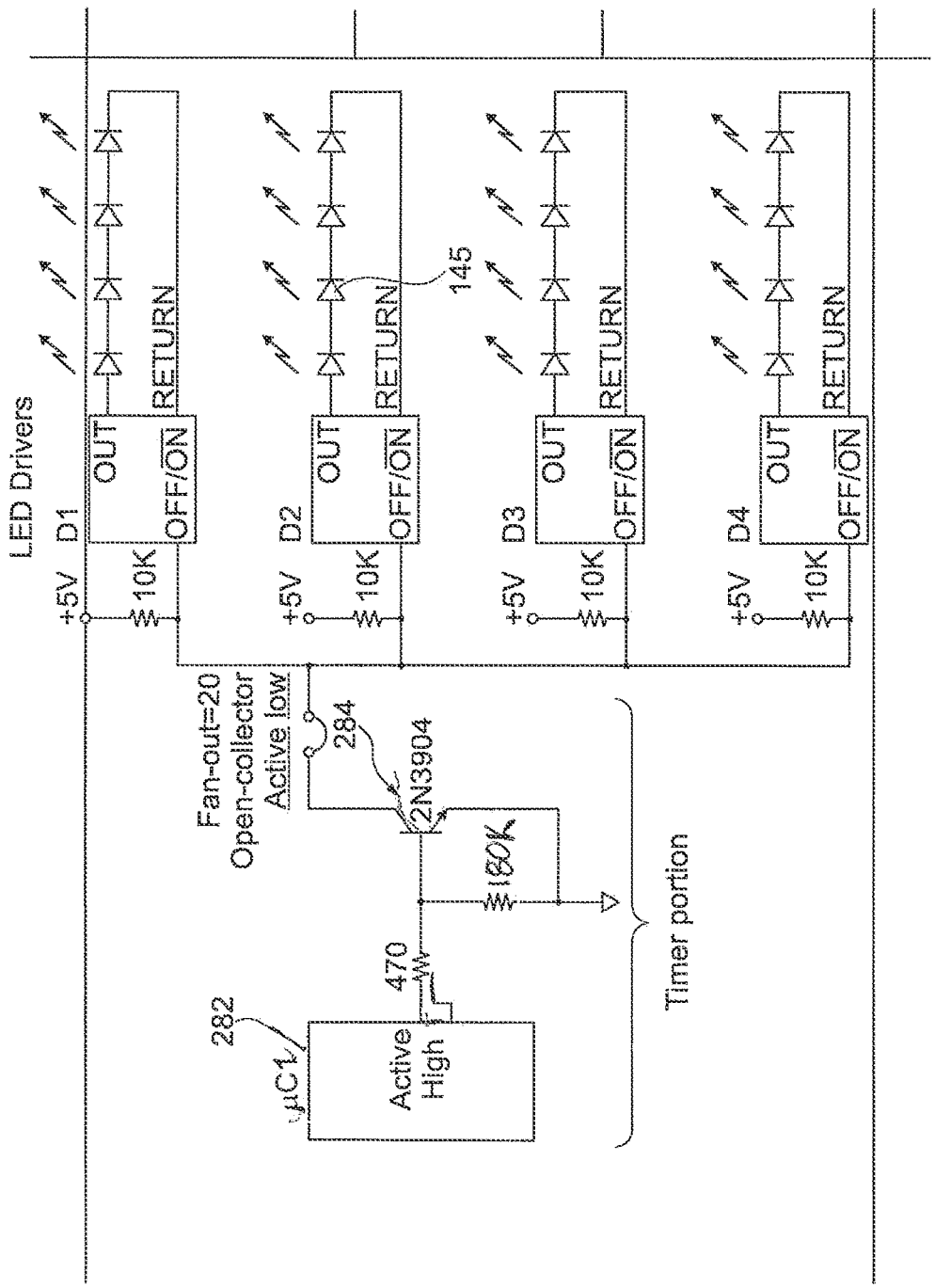
FIG. 18 is a circuit diagram of the timer portion of the timer circuit for the portable lamp assembly of the present invention.

As shown in FIG. 18, the plurality of light emitting diodes 145 may be connected in a series and/or parallel fashion. Individual ballast resistors are not required, since the LED drivers shown in FIG. 16 determine the current in any series chain of four light emitting diodes 145. It is contemplated that more or less light emitting diodes could be present in any series chain depending on the compliance of the LED driver.

As illustrated in FIG. 1, the portable lamp assembly 100 can be situated in a closed position for moving and storage. As shown, the angle between the spine member bottom side 112 and each of the first side panel bottom side 128 and the second side panel bottom side 144 is equal to or exceeds 90 degrees. Therefore, when the portable lamp assembly 100 is not in use, the portable lamp assembly 100 can be readily folded up and stored. In the event that the portable lamp assembly 100 is carried (to another room) while set up for a patient, the prior art device experienced the potential to collapse under its own weight, especially in the sub-case of body treatment. In the case of the portable lamp assembly 100 of the present disclosure, the upper pivot points provided by the block detent assembly 166 are further provided with discrete positions defined by a ball detent that can withstand the torque of carrying the portable lamp assembly 100 while set up.

The portable lamp assembly 100 also has a partially open position as illustrated for treating heads, scalps, arms, legs, hands and feet of a patient, as shown in FIG. 2. The torque required in the prior art lower hinge to maintain stability made it difficult for the operator to overcome to obtain a fine adjustment. Also, the upper and lower pivot points were very difficult to adjust independently. They naturally interact. In the case of the portable lamp assembly 100 of the present disclosure, angle and height are discrete, independent, and simple to adjust.

According to the present disclosure, the tangent links 190, 200 ensure a positive lock at one of several discrete heights. Cleats 210 are added to ensure that the tangent links 190, 200 remain vertical relative to the examination or treatment table. Each cleat 210 contacting the examination or treatment table may be provided with rubber bumpers for a sure grip. Also, the block detent assembly 166 provides discrete detent positions to allow accurate angle setting between each side panel 104, 106 and the central control box 108 housed in the spine member 102. It thus offers independent height setting for better patient fitting, with notches 226 and rotational positions that can be marked for often used set-up repetition.

During use of the portable lamp assembly 100 for treating the face of the patient, a head of the patient can rest on a disposable exam paper, which in turn rests on an examination or treatment table. Light propagates from the spine member 102, the first side panel 104, and the second side panel 106. An air space is maintained between a surface of the head of the patient and a surface of the lamps. In these configurations, the size of the air space is adjustable via the block detent assemblies 166 and the first and second tangent links 190, 200.

Finally, the portable lamp assembly 100 includes a fully open position as illustrated in FIG. 3 for treating chests and backs of patients. The portable lamp assembly 100 can be held in any partially or fully open position by means of the block detent assemblies 166 and the first and second tangent links 190, 200. The prior art unit provided very limited height adjustment for body treatment. The portable lamp assembly 100 of the present disclosure provides this adjustment over a wide range.

The portability of the portable lamp assembly 100 of the present disclosure is enhanced due to its light weight, which is expected to weigh no more than 12 pounds, due to its easy foldability to increase its compactness for storage, and due to its compact folded size (expected to be 12 inches (30 cm) long, 12 inches (30 cm) high, and 5 inches (13 cm) wide). It is comparable in size to a large three ring binder when folded and can be stored on a bookshelf, counter, or desk. It can also be produced and manufactured at a relatively low cost.

Thus, in operation, the benefits of the portable lamp assembly 100 of the present disclosure include: (1) increased overall stability; (2) discrete height adjustment; (3) height adjustment over a wide range for body treatment; (4) discrete angle adjustment; (5) independence of discrete height and discrete angle adjustment; (6) attainment of static stability above patient with a disturbance load applied; and (7) attainment of static stability as the portable lamp assembly 100 is carried to another room while set up.

The portable lamp assembly 100 of the present disclosure thus presents a mechanically self-supporting device, with no stand required. It is adaptable for treating patients in a comfortable, supine position for all modalities, while also used not only to treat full face (including ears), but can also be used to treat the scalp, back, upper chest, and other large areas. It has a dedicated patient cooling fan on a flexible hinge to increase comfort.

Various alterations to the methods of treatment using the portable lamp assembly 100 and the construction of the portable lamp assembly are contemplated. For example, it is contemplated that: (1) the arm, leg, hand or foot of a patient can be raised above the examination or treatment table with a folded towel, pillow or pad; (2) the number of light emitting diodes 145 can vary depending on the size and location of the area being treated; and (3) a clip could be added to one or both side panels 104, 106 for holding a patient chart. Other modifications are also contemplated.

It will be understood by one having ordinary skill in the art that construction of the present disclosure and other components is not limited to any specific material. Other exemplary embodiments of the disclosure disclosed herein may be formed from a wide variety of materials, unless described otherwise herein.

For purposes of this disclosure, the term "coupled" or "operably coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

For purposes of this disclosure, the term "connected" or "operably connected" (in all of its forms, connect, connecting, connected, etc.) generally means that one component functions with respect to another component, even if there are other components located between the first and second component, and the term "operable" defines a functional relationship between components.

It is also important to note that the construction and arrangement of the elements of the present disclosure as shown in the exemplary embodiments is illustrative only. Although only a few embodiments of the present innovations have been described in detail in this disclosure, those skilled in the art who review this disclosure will readily appreciate that, unless otherwise described, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating positions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

We claim:

1. A portable lamp assembly comprising:
a spine member having a spine member top side and a spine member bottom side, the spine member including at least one spine member source of light connected to the spine member bottom side of the spine member, the spine member also including a first side and a second side;
a first side panel having a proximal edge operably and rotatably coupled to the first side of the spine member, the first side panel including a first side panel top side and a first side panel bottom side, the first side panel including at least one first side source of light connected to the first side panel bottom side of the first side panel;
a first tangent link prismatically and rotatably operably coupled to the first side panel, the first tangent link having a lower portion at a distal end thereof for support of the first side panel on a surface, an upper portion, and a plurality of vertical adjustment positions disposed between the upper portion and the lower portion;
a second side panel having a proximal edge operably and rotatably coupled to the second side of the spine member, the second side panel including a second side panel top side and a second side panel bottom side, the second side panel including at least one second side source of light connected to the second side panel bottom side of the second side panel;
a second tangent link prismatically and rotatably operably coupled to the second side panel, the second tangent link having a lower portion at a distal end thereof for support of the second side panel on the surface, an upper portion, and a plurality of vertical adjustment positions disposed between the upper portion and the lower portion;
wherein the first side panel and the second side panel can be rotated in a first direction relative to the spine member to arrange the portable lamp assembly in an open position to allow the at least one spine member source of light, the at least one first side source of light and the at least one second side source of light to emit light towards a target area;

wherein the first side panel and the second side panel can be rotated in a second direction relative to the spine member to arrange the portable lamp assembly in a closed position for storage of the portable lamp assembly;

wherein the portable lamp assembly is free standing in the open position to allow the portable lamp assembly to be used without any external support; and wherein a relative height of each of the first side panel and the second side panel relative the surface may adjusted by selection of a one of the plurality of vertical adjustment positions of each of the first and second tangent links.

2. The portable lamp assembly of claim 1, further comprising:
a pair of first tangent links attached to the first side panel between the upper portion and lower portion of the pair of first tangent links, whereby each of the first tangent links is prismatically and rotatably operably coupled to a one of a pair of opposite sides of first side panel; and
a pair of second tangent links attached to the second side panel between the upper portion and lower portion of the pair of second tangent links, whereby each of the second tangent links is prismatically and rotatably operably coupled to a one of a pair of opposite sides of the second side panel.

3. The portable lamp assembly of claim 2, wherein each of the pairs of first and second tangent links are first mirror image of each other.

4. The portable lamp assembly of claim 3, further comprising a first upper crosslink member extending between the upper portion of each of the pair of first tangent links and a first lower crosslink member extending between the lower portion of each of the pair of first tangent links; and
a second upper crosslink member extending between the upper portion of each of the pair of second tangent links and a second lower crosslink member extending between the lower portion of each of the pair of second tangent links.

5. The portable lamp assembly of claim 4, further comprising a resilient clip disposed on each of an upper portion of the first side panel top side and the second side panel top side, wherein the first and second upper crosslink members are retained by the clips on in a stored position.

6. The portable lamp assembly of claim 5, further comprising a pair of spaced resilient clips disposed on each of an upper portion of the first side panel top side and the second side panel top side, wherein the first and second upper crosslink members are retained by the pair of clips on in a stored position.

7. The portable lamp assembly of claim 3, further comprising a plurality of pivot mounts, wherein a one of the plurality of pivot mounts is disposed on each of the one of a pair of opposite edges of the first side panel and on each of the one of a pair of opposite sides of the second side panel, wherein the plurality of pivot mounts engages a one of the plurality of vertical adjustment positions disposed between the upper portion and the lower portions of the pairs of first and second tangent links.

8. The portable lamp assembly of claim 7, wherein the plurality of vertical adjustment positions disposed between the upper portion and the lower portions of the pairs of first and second tangent links comprises a vertically extending slot and a plurality of inwardly and downwardly inclined notches extending from the vertically extending slot, wherein the plurality of pivot mounts are disposed within the vertically extending slot for movement of the pairs of first and second tangent links relative the first side panel or the second side panel and the plurality of pivot mounts are selectively disposed within one of the plurality of notches for securing the one of the pairs of first and second tangent links relative the first side panel or the second side panel when the portable lamp assembly is in use.

9. The portable lamp assembly of claim 7, wherein the plurality of pivot mounts each comprise outwardly extending pins.

10. The portable lamp assembly of claim 7, wherein the plurality of pivot mounts each comprise a threaded and rotatable knob extending into a threaded opening on each of the opposite sides of the first side panel and on each of the one of a pair of opposite sides of the second side panel to releasably secure the first and second tangent links to the first side panel and the second side panel.

11. The portable lamp assembly of claim 7, wherein the plurality of pivot mounts comprise a retaining clamp extending through each of the first and second side panels, the retaining clamp further comprising a longitudinally extending bar, a retaining stop threaded onto a first distal end of the bar, and a clamp member threaded onto a proximal end of the bar, wherein the clamp member includes a base having curvilinear recess and a rotatable handle having a curvilinear pivot mount;
wherein the bar is inserted through each of the plurality of vertical adjustment positions disposed on the first and second tangent links and through the first side panel and the second side panel, the retaining stop and/or clamp member are threaded onto the bar until snug, and the rotatable handle is rotated to clamp and lock the first and second tangent links relative the first side panel and the second side panel.

12. The portable lamp assembly of claim 1, wherein the lower portion of each of the first and second tangent links comprises a cleat extending orthogonally with respect to a vertical longitudinal axis of the first and second tangent links.

13. The portable lamp assembly of claim 12, wherein the cleat is rotatably and operably coupled with the lower portion of each of the first and second tangent links and is rotatable between a first position extending orthogonally with respect to the vertical longitudinal axis of the first and second tangent links and a second position extending upwardly and parallel to the vertical longitudinal axis of the first and second tangent links.

14. The portable lamp assembly of claim 1, further comprising a patient fan assembly rotatably and operably coupled with an end of the spine member for providing a user with air ventilation.

15. The portable lamp assembly of claim 14, wherein the patient fan assembly is operably coupled with the spine member with adjustable torque hinges.

16. The portable lamp assembly of claim 1, wherein each of the first side panel and the second side panel is rotatably and operably coupled to the spine member by a pair of block detent assemblies.

17. The portable lamp assembly of claim 16, wherein each of the pair of block detent assemblies comprises:
a plurality of recesses arranging in a semi-circular pattern disposed on the spine member or proximate the proximal side of each of the first side panel or the second side panel; and
a spring loaded detent disposed on the other of the spine member or proximate the proximal side of each of the first side panel or the second side panel;

wherein the detent is selectively disposed within one of the plurality of recesses for securing the spine member relative the first side panel and the second side panel when the portable lamp assembly is in use.

18. The portable lamp assembly of claim 17, wherein a unique position indicia is disposed proximate each of the plurality of vertical adjustment positions of the first and second tangent links and each of the plurality of recesses of the block detent assemblies.

19. The portable lamp assembly of claim 18, wherein the unique position indicia is disposed proximate each of the plurality of vertical adjustment positions of the first and second tangent links is a visible number and the unique position indicia proximate each of the plurality of recesses of the block detent assemblies is a visible alphabetic letter.

20. The portable lamp assembly of claim 1, wherein the at least one spine member source of light, the at least one first side source of light and the at least one second side source of light each comprise light emitting diodes.

21. The portable lamp assembly of claim 20, further comprising a constant current source electronic circuit to drive a plurality of light emitting diodes.

22. The portable lamp assembly of claim 20, further comprising a low-level signal light emitting diode on-off enable line switching capability.

23. The portable lamp assembly of claim 20, further comprising a plurality of rows of the light emitting diodes on each of the first side panel bottom side of the first side panel and the second side panel bottom side of the second side panel, wherein a power intensity of one of the plurality of rows of the light emitting diodes is individually adjustable.

24. The portable lamp assembly of claim 23, wherein the power intensity of the one of the plurality of rows of light emitting diodes is individually adjustable by a potentiometer accessible by an opening on the first side panel top side of the first side panel and the second side panel top side of the second side panel.

25. The portable lamp assembly of claim 1, further comprising a pair of cooling fan assemblies, one each of the pair of cooling fan assemblies disposed on each the first top side and the second top side of each of the first side panel and the second side panel, whereby cooling air is directed to the one first side source of light and the one second side source of light.

26. The portable lamp assembly of claim 1, further including:
a digital timer connected to the spine member, the first side panel or the second side panel to display and control a duration of light exposure.

27. The portable lamp assembly of claim 1, further including:
a counter connected to the spine member, the first side panel or the second side panel to record and display the number of hours that the spine light source, the first side source of light, or the second side source of light sources have been powered.

28. The portable lamp assembly of claim 1, further comprising a pair of handles, one each of the pair of handles disposed on a lower portion of each the first top side and the second top side of each of the first side panel and the second side panel, whereby each of the first side panel and the second side panel may be manipulated between an open position with the lower portion of the first tangent link and the second tangent link resting on a support surface and with the spine member, the first side panel and the second side panel being spaced from the support surface.

29. The portable lamp assembly of claim 1, wherein the at least one spine member source of light connected to the spine member bottom side of the spine member, the one first side source of light connected to the first side panel bottom side of the first side panel, or the one second side source of light connected to the second side panel bottom side of the second side panel emits light in a red electromagnetic spectrum of wavelengths between 550-750 nm.

30. The portable lamp assembly of claim 29, wherein the at least one spine member source of light connected to the spine member bottom side of the spine member, the one first side source of light connected to the first side panel bottom side of the first side panel, or the one second side source of light connected to the second side panel bottom side of the second side panel emits light at an electromagnetic wavelength of substantially 630 nm.

31. The portable lamp assembly of claim 1, wherein the at least one spine member source of light connected to the spine member bottom side of the spine member, the one first side source of light connected to the first side panel bottom side of the first side panel, or the one second side source of light connected to the second side panel bottom side of the second side panel emits light in a blue electromagnetic spectrum of wavelengths between 350-450 nm.

32. The portable lamp assembly of claim 1, wherein the at least one spine member source of light connected to the spine member bottom side of the spine member, the one first side source of light connected to the first side panel bottom side of the first side panel, or the one second side source of light connected to the second side panel bottom side of the second side panel emits light at an electromagnetic wavelength of substantially 415 nm.

33. The portable lamp assembly of claim 1, wherein the at least one spine member source of light connected to the spine member bottom side of the spine member, the one first side source of light connected to the first side panel bottom side of the first side panel, or the one second side source of light connected to the second side panel bottom side of the second side panel emits light at a power intensity of about 60 mW/cm$^2$, +/−15%.

34. The portable lamp assembly of claim 1, wherein the at least one spine member source of light connected to the spine member bottom side of the spine member, the one first side source of light connected to the first side panel bottom side of the first side panel, or the one second side source of light connected to the second side panel bottom side of the second side panel emits light at a power intensity of about 10 mW/cm$^2$, +/−15%.

35. The portable lamp assembly of claim 1, wherein an angle between the spine member bottom side of the spine member and each of the first side panel bottom side and the second side panel bottom side is equal to or exceeds 90 degrees.

36. The portable lamp assembly of claim 1, further including a human phantom with multiple photodetectors to display and/or control the intensity of light exposure as a function of position on the skin surface of the patient.

37. The portable lamp assembly of claim 1, further including a proximity sensor connected to the spine member, the first side panel or the second side panel to display the distance between the light source optics and the skin surface of the patient.

38. A portable lamp assembly comprising:
a spine member having a spine member top side and a spine member bottom side, the spine member including at least one spine member source of light connected to the spine member bottom side of the spine member, the spine member also including a first side and a second side;

a first side panel rotatably connected to the first side of the spine member, the first side panel including a first side panel top side and a first side panel bottom side, the first side panel including at least one first side source of light connected to the first side panel bottom side of the first side panel;

a second side panel rotatably connected to the second side of the spine member, the second side panel including a second side panel top side and a second side panel bottom side, the second side panel including at least one second side source of light connected to the second side panel bottom side of the second side panel;

a pair of first tangent links attached to the first side panel between an upper portion and a lower portion of the pair of first tangent links, whereby each of the first tangent links is prismatically and rotatably operably coupled to a one of a pair of opposite sides of first side panel; and a pair of second tangent links attached to the second side panel between the upper portion and a lower portion of the pair of second tangent links, whereby each of the second tangent links is prismatically and rotatably operably coupled to a one of a pair of opposite sides of the second side panel;

wherein the portable lamp assembly can be placed in an open position with the lower portion of the first tangent link and the second tangent link resting on a support surface and with the spine member, the first side panel and the second side panel being spaced from the support surface.

39. A portable lamp assembly comprising:

a spine member having a spine member top side and a spine member bottom side, the spine member including at least one spine member source of light connected to the spine member bottom side of the spine member, the spine member also including a first side and a second side;

a first side panel rotatably connected to the first side of the spine member, the first side panel including a first side panel top side and a first side panel bottom side, the first side panel including at least one first side source of light connected to the first side panel bottom side of the first side panel;

a second side panel rotatably connected to the second side of the spine member, the second side panel including a second side panel top side and a second side panel bottom side, the second side panel including at least one second side source of light connected to the second side panel bottom side of the second side panel;

a pair of first tangent links attached to the first side panel between an upper portion and a lower portion of the pair of first tangent links, whereby each of the first tangent links is prismatically and rotatably operably coupled to a one of a pair of opposite sides of first side panel, and the first tangent link has a lower portion at a distal end thereof for support of the first side panel on a surface, an upper portion, and a plurality of vertical adjustment positions disposed between the upper portion and the lower portion;

a pair of second tangent links attached to the second side panel between the upper portion and a lower portion of the pair of second tangent links, whereby each of the second tangent links is prismatically and rotatably operably coupled to a one of a pair of opposite sides of the second side panel, and the second tangent link has a lower portion at a distal end thereof for support of the first side panel on the surface, an upper portion, and a plurality of vertical adjustment positions disposed between the upper portion and the lower portion; and a pair of block detent assemblies by which the first side panel and the second side panel are rotatably and operably coupled is to the spine member, the pair of block detent assemblies comprising a plurality of recesses arranging in a semi-circular pattern disposed on the spine member or proximate the proximal side of each of the first side panel or the second side panel;

and a spring loaded detent disposed on the other of the spine member or proximate the proximal side of each of the first side panel or the second side panel;

wherein the portable lamp assembly can be placed in an open position with the lower portion of the first tangent link and the second tangent link resting on a support surface and with the spine member, the first side panel and the second side panel being spaced from the support surface, and wherein a relative height of each of the first side panel and the second side panel relative the surface may adjusted by selection of a one of the plurality of vertical adjustment positions of each of the first and second tangent links; and wherein the detent is selectively disposed within one of the plurality of recesses for securing the spine member relative the first side panel and the second side panel when the portable lamp assembly is in use.

* * * * *

UNITED STATES PATENT AND TRADEMARK OFFICE
CERTIFICATE OF CORRECTION

PATENT NO. : 11,333,336 B1
APPLICATION NO. : 17/412779
DATED : May 17, 2022
INVENTOR(S) : Tobin et al.

Page 1 of 1

It is certified that error appears in the above-identified patent and that said Letters Patent is hereby corrected as shown below:

In the Specification

Column 4, Line 55, "2⅝ inch" should be --2¾ inches--.

Column 4, Line 56, "7⅝ inch" should be --7¾ inches--.

Signed and Sealed this
Thirteenth Day of September, 2022

Katherine Kelly Vidal
*Director of the United States Patent and Trademark Office*